(12) United States Patent
Lin et al.

(10) Patent No.: US 11,622,693 B2
(45) Date of Patent: Apr. 11, 2023

(54) METHOD AND APPARATUS FOR NON-CONTACT FAST VITAL SIGN ACQUISITION BASED ON RADAR SIGNAL

(71) Applicant: University of Florida Research Foundation, Inc., Gainesville, FL (US)

(72) Inventors: Jenshan Lin, Gainesville, FL (US); Changyu Wei, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 91 days.

(21) Appl. No.: 17/363,857

(22) Filed: Jun. 30, 2021

(65) Prior Publication Data

US 2021/0321879 A1 Oct. 21, 2021

Related U.S. Application Data

(63) Continuation of application No. 15/517,214, filed as application No. PCT/US2015/054669 on Oct. 8, 2015, now Pat. No. 11,051,702.

(Continued)

(51) Int. Cl.
*A61B 5/0205* (2006.01)
*A61B 5/00* (2006.01)
(Continued)

(52) U.S. Cl.
CPC .............. *A61B 5/0205* (2013.01); *A61B 5/05* (2013.01); *A61B 5/113* (2013.01); *A61B 5/7207* (2013.01);
(Continued)

(58) Field of Classification Search
CPC ......... A61B 5/0205; A61B 5/05; A61B 5/113; A61B 5/7207; A61B 5/7214;
(Continued)

(56) References Cited

U.S. PATENT DOCUMENTS

| 3,796,208 A | 3/1974 | Bloice |
| 4,085,740 A | 4/1978 | Allen, Jr. |

(Continued)

FOREIGN PATENT DOCUMENTS

| EP | 1058451 | 12/2000 |
| GB | 2099257 | 12/1982 |

(Continued)

OTHER PUBLICATIONS

Droitcour, A., et al., "Range Correlation and I/Q Performance Benefits in Single-Chip Silicon Doppler Radars for Noncontact Cadiopulmonary Monitoring". IEEE Transactions on Microwave Theory and Techniques, 52(3). Mar. 2004, p. 838-848 (Year: 2004).*

(Continued)

*Primary Examiner* — Keith M Raymond
*Assistant Examiner* — Sean A Frith
(74) *Attorney, Agent, or Firm* — Thomas | Horstemeyer, LLP

(57) ABSTRACT

Various examples are provided for non-contact vital sign acquisition. Information can be provided regarding vibrations of a target using a radar signal such as, e.g., non-contact vital sign measurement. Examples include estimation of heart rate, change in heart rate, respiration rate, and/or change in respiration rate, for a human or other animal. Implementations can produce one or both rates of vibration and/or change in one or both rates of vibration for a target other than an animal or human experiencing two vibrations at the same time, such as a motor, a vehicle incorporating a motor, or another physical object. Some implementations can estimate the respiration movement in the radar baseband output signal. The estimated respiration signal can then be subtracted from radar signals in the time domain and, optionally, can be further enhanced using (Continued)

digital signal processing techniques, to produce an estimate of the heartbeat pulses.

20 Claims, 16 Drawing Sheets

Related U.S. Application Data

(60) Provisional application No. 62/061,320, filed on Oct. 8, 2014.

(51) Int. Cl.
    *A61B 5/05*         (2021.01)
    *A61B 5/113*       (2006.01)
    *A61B 8/02*         (2006.01)
    *A61B 8/08*         (2006.01)
    *G01S 7/41*         (2006.01)
    *G01S 7/35*         (2006.01)
    *G01S 13/58*       (2006.01)
    *G01S 13/88*       (2006.01)
    *A61B 5/11*         (2006.01)

(52) U.S. Cl.
    CPC .......... *A61B 5/7214* (2013.01); *A61B 5/7239* (2013.01); *A61B 5/7282* (2013.01); *A61B 8/02* (2013.01); *A61B 8/5223* (2013.01); *G01S 7/354* (2013.01); *G01S 7/415* (2013.01); *G01S 13/583* (2013.01); *G01S 13/88* (2013.01); *A61B 5/0006* (2013.01); *A61B 5/0015* (2013.01); *A61B 5/1102* (2013.01); *A61B 2503/40* (2013.01); *G01S 7/358* (2021.05)

(58) Field of Classification Search
    CPC ....... A61B 5/7239; A61B 5/7282; A61B 8/02; A61B 8/5223; A61B 5/0006; A61B 5/0015; A61B 5/1102; A61B 2503/40; G01S 7/354; G01S 7/415; G01S 13/583; G01S 13/88; G01S 7/358
    See application file for complete search history.

(56) References Cited

U.S. PATENT DOCUMENTS

| | | | |
|---|---|---|---|
| 4,357,944 A | 11/1982 | Mauser et al. |
| 4,378,698 A | 4/1983 | Masse et al. |
| 4,513,748 A | 4/1985 | Nowogrodzki et al. |
| 5,507,291 A | 4/1996 | Stirbl et al. |
| 5,647,834 A | 7/1997 | Ron |
| 5,694,093 A | 12/1997 | Dasilva et al. |
| 5,867,257 A | 2/1999 | Rice et al. |
| 6,006,188 A | 12/1999 | Bogdashevsky et al. |
| 6,064,383 A | 5/2000 | Skelly |
| 6,132,371 A | 10/2000 | Dempsey et al. |
| 6,188,220 B1 | 2/2001 | Schaefer |
| 6,219,657 B1 | 4/2001 | Hatayama |
| 6,275,806 B1 | 8/2001 | Petrushin |
| 6,480,826 B2 | 11/2002 | Petrushin |
| 6,697,457 B2 | 2/2004 | Petrushin |
| 6,728,679 B1 | 4/2004 | Strubbe et al. |
| 6,768,938 B2 | 7/2004 | McBrien et al. |
| 6,931,341 B2 | 8/2005 | Wakabayashi et al. |
| 7,043,008 B1 | 5/2006 | Dewan |
| 7,073,384 B1 | 7/2006 | Donskoy et al. |
| 7,116,426 B2 | 10/2006 | Lal et al. |
| 7,138,905 B2 | 11/2006 | Pavlidis et al. |
| 7,165,033 B1 | 1/2007 | Liberman |
| 7,272,431 B2 | 9/2007 | McGrath |
| 7,373,301 B2 | 5/2008 | Kemp et al. |
| 7,401,020 B2 | 7/2008 | Eide |
| 7,451,079 B2 | 11/2008 | Oudeyer |
| 7,477,398 B2 | 1/2009 | Lal et al. |
| 7,606,701 B2 | 10/2009 | Degani et al. |
| 7,627,475 B2 | 12/2009 | Petrushin |
| 7,809,117 B2 | 10/2010 | Runge et al. |
| 7,817,082 B2 | 10/2010 | Dwelly et al. |
| 7,848,896 B2 | 12/2010 | Li et al. |
| 7,903,020 B2 | 3/2011 | Lin et al. |
| 7,914,468 B2 | 3/2011 | Shalon et al. |
| 8,052,600 B2 | 11/2011 | Beck et al. |
| 8,239,000 B1 | 8/2012 | Morris et al. |
| 8,306,610 B2 | 11/2012 | Mirow |
| 8,652,040 B2 | 2/2014 | LeBoeuf et al. |
| 8,721,554 B2 | 5/2014 | Lin et al. |
| 8,814,805 B2 | 8/2014 | Lin et al. |
| 9,200,945 B2 | 12/2015 | Lin et al. |
| 9,477,812 B2 | 10/2016 | Lin et al. |
| 2002/0002464 A1 | 1/2002 | Petrushin |
| 2002/0007119 A1 | 1/2002 | Pelissier |
| 2002/0065466 A1 | 5/2002 | Rather et al. |
| 2002/0101568 A1 | 8/2002 | Eberl et al. |
| 2002/0139842 A1 | 10/2002 | Swaine |
| 2003/0028384 A1 | 2/2003 | Kemp et al. |
| 2003/0055654 A1 | 3/2003 | Oudeyer |
| 2003/0069728 A1 | 4/2003 | Tato et al. |
| 2003/0093280 A1 | 5/2003 | Oudeyer |
| 2003/0163311 A1 | 8/2003 | Gong |
| 2003/0182117 A1 | 9/2003 | Monchi et al. |
| 2003/0187660 A1 | 10/2003 | Gong |
| 2003/0208113 A1 | 11/2003 | Mault et al. |
| 2004/0039282 A1 | 2/2004 | Szabo et al. |
| 2004/0123667 A1 | 7/2004 | McGrath |
| 2004/0141417 A1 | 7/2004 | Wakabayashi et al. |
| 2004/0167774 A1 | 8/2004 | Shrivastav |
| 2004/0181143 A1 | 9/2004 | Israel |
| 2004/0249258 A1 | 12/2004 | Tupin et al. |
| 2004/0249634 A1 | 12/2004 | Degani et al. |
| 2005/0033127 A1 | 2/2005 | Ciurczak et al. |
| 2005/0073424 A1 | 4/2005 | Ruoss et al. |
| 2005/0088981 A1 | 4/2005 | Woodruff et al. |
| 2005/0128123 A1 | 6/2005 | Greneker, III et al. |
| 2005/0131273 A1 | 6/2005 | Asano et al. |
| 2005/0154264 A1 | 7/2005 | Lecompte et al. |
| 2005/0163302 A1 | 7/2005 | Mock et al. |
| 2005/0171411 A1 | 8/2005 | KenKnight et al. |
| 2006/0028556 A1 | 2/2006 | Bunn et al. |
| 2006/0058694 A1 | 3/2006 | Clark et al. |
| 2006/0064037 A1 | 3/2006 | Shalon et al. |
| 2006/0122834 A1 | 6/2006 | Bennett |
| 2006/0209631 A1 | 9/2006 | Melese et al. |
| 2006/0224046 A1 | 10/2006 | Ramadas et al. |
| 2007/0066916 A1 | 3/2007 | Lemos |
| 2007/0093702 A1 | 4/2007 | Yu et al. |
| 2007/0149883 A1* | 6/2007 | Yesha ................. A61B 5/6892 |
| | | | 600/485 |
| 2007/0162505 A1 | 7/2007 | Cecchi et al. |
| 2007/0186165 A1 | 8/2007 | Maislos et al. |
| 2007/0192108 A1 | 8/2007 | Konchitsky |
| 2007/0183604 A1 | 9/2007 | Araki et al. |
| 2007/0208569 A1 | 9/2007 | Subramanian et al. |
| 2007/0265531 A1 | 11/2007 | He et al. |
| 2007/0270659 A1 | 11/2007 | Giegerich |
| 2008/0045805 A1 | 2/2008 | Sarel et al. |
| 2008/0045832 A1 | 2/2008 | McGrath |
| 2008/0074307 A1 | 3/2008 | Boric-Lubecke et al. |
| 2008/0077015 A1 | 3/2008 | Boric-Lubecke et al. |
| 2008/0162352 A1 | 7/2008 | Gizewski |
| 2008/0188752 A1 | 8/2008 | Randall et al. |
| 2008/0208015 A1 | 8/2008 | Morris et al. |
| 2008/0215617 A1 | 9/2008 | Cecchi et al. |
| 2008/0238757 A1 | 10/2008 | Lin et al. |
| 2008/0260212 A1 | 10/2008 | Moskal et al. |
| 2008/0269589 A1 | 10/2008 | Thijs et al. |
| 2008/0300805 A1 | 12/2008 | Li et al. |
| 2008/0302187 A1 | 12/2008 | Huber et al. |
| 2009/0063154 A1 | 3/2009 | Gusikhin et al. |
| 2009/0076343 A1 | 3/2009 | James et al. |
| 2009/0128567 A1 | 5/2009 | Shuster et al. |
| 2009/0156907 A1 | 6/2009 | Jung et al. |
| 2009/0176257 A1 | 7/2009 | Bahn et al. |
| 2009/0203972 A1 | 8/2009 | Heneghan et al. |

(56) References Cited

U.S. PATENT DOCUMENTS

| | | | |
|---|---|---|---|
| 2009/0216093 A1 | 8/2009 | Sebastian | |
| 2009/0292180 A1 | 11/2009 | Mirow | |
| 2009/0313019 A1 | 12/2009 | Kato et al. | |
| 2010/0083320 A1 | 4/2010 | Roberts et al. | |
| 2010/0130873 A1 | 5/2010 | Yuen et al. | |
| 2010/0158331 A1 | 6/2010 | Jacobs et al. | |
| 2010/0179438 A1 | 7/2010 | Heneghan et al. | |
| 2010/0198083 A1 | 8/2010 | Lin et al. | |
| 2010/0204587 A1 | 8/2010 | Lin et al. | |
| 2010/0205541 A1 | 8/2010 | Rapaport et al. | |
| 2010/0226504 A1 | 9/2010 | Watanabe | |
| 2010/0241009 A1* | 9/2010 | Petkie | G01S 7/35 342/147 |
| 2010/0241010 A1* | 9/2010 | Lin | G01S 13/56 600/484 |
| 2010/0281986 A1 | 11/2010 | Toal et al. | |
| 2011/0060215 A1 | 3/2011 | Tupin et al. | |
| 2011/0183305 A1 | 7/2011 | Orbach | |
| 2011/0257536 A1* | 10/2011 | Ser | A61B 5/0205 600/484 |
| 2011/0288379 A1 | 11/2011 | Wu | |
| 2012/0022348 A1 | 1/2012 | Droitcour | |
| 2013/0245437 A1* | 9/2013 | Gamble | A61B 5/02405 600/430 |
| 2014/0024917 A1* | 1/2014 | McMahon | G01S 13/18 600/407 |
| 2014/0128748 A1* | 5/2014 | Horng | G08B 13/2491 600/484 |
| 2015/0241555 A1 | 8/2015 | Lin et al. | |
| 2016/0336989 A1 | 11/2016 | Lin et al. | |
| 2016/0374622 A1 | 12/2016 | Lin et al. | |

FOREIGN PATENT DOCUMENTS

| | | |
|---|---|---|
| JP | 2006055504 | 3/2006 |
| JP | 2007-010373 | 1/2007 |
| SU | 1337875 | 9/1987 |
| WO | 2004/013611 | 2/2004 |
| WO | 2007/010460 | 1/2007 |
| WO | 2008/151141 | 12/2008 |
| WO | 2009/009690 | 1/2009 |
| WO | 2009/009722 | 1/2009 |
| WO | 2009/076298 | 6/2009 |
| WO | 2010/148141 | 12/2010 |

OTHER PUBLICATIONS

Blum, T.E., et al., "Advances in Laboratory Modeling of Wave Propagation," Optical Engineering, Oct. 24, 2006, Article No. 10430.

Castellini, P., et al., "Laser Doppler Vibrometry: Development of Advanced Solutions Answering to Technology's Needs," Mechanical Systems and Signal Processing, Aug. 2006, vol. 20, No. 6, pp. 1265-1285.

Ivanov, E.N., et al., "Microwave Interferometry: Application to Precision Measurements and Noise Reductions Techniques," IEEE Transactions on Ultrasonics, Ferroelectrics, and Frequency Control, Nov. 1998, vol. 45, No. 6, pp. 1526-1536.

Kim, S., et al., "On the Development of a Multifunction Millimeter-Wave Sensor for Displacement Sensing and Low-Velocity Measurement," IEEE Transactions on Microwave Theory and Techniques, Nov. 2004, vol. 52, No. 11, pp. 2503-2512.

Lai, S.H.Y., "Engine System Diagnosis Using Vibration Data," Computers and Industrial Engineering, Sep. 1993, vol. 25, Nos. 1-4, pp. 135-138.

Li, C., et al., "Non-Contact Measurement of Periodic Movements by a 22-40GHz Radar Sensor Using Nonlinear Phase Modulation," IEEE/MTT-S International Microwave Symposium, Honolulu, HI, Jun. 2007, pp. 579-582.

MacPherson, W.N., et al., "Multipoint Laser Vibrometer for Modal Analysis," Applied Optics, Jun. 2007, vol. 46, No. 16, pp. 3126-3132.

Stelzer, A., et al., "A Microwave Position Sensor with Sub-Millimeter Accuracy," IEEE Transactions on Microwave Theory and Techniques, Dec. 1999, vol. 47, No. 12, pp. 2621-2624.

Yan, Y., et al., "Effects of I/Q Mismatch on Measurement of Periodic Movement Using a Doppler Radar Sensor," IEEE Radio and Wireless Symposium, 2010, pp. 196-199.

Yan, Y., et al., "Ka-band Quadrature Doppler Radar System with Sub-millimeter Resolution and Sensitivity in Measuring Periodic Movement," 11 1th Annual IEEE Wireless and Microwave Technology Conference, Apr. 2010, pp. 12-13.

Yan, Y., et al., "Wavelength Division Sensing RF Vibrometer," IEEE/MTT-S International Microwave Symposium, Baltimore, MD, Jun. 2011.

Yoshizumi, N., et al., "Multiple-Frequency Ultrasonic Imaging by Transmitting Pulsed Waves of Two Frequencies," Journal of Medical Ultrasonics, Jun. 2009, vol. 36, No. 2, pp. 53-60.

Yan, Y., et al.; Analysis of Detection Methods of RF Vibrometer for Complex Motion Measurement; IEEE Transactions on Microwave Theory and Techniques, vol. 59, No. 12, Dec. 2011; p. 3556-3566.

Cao, Y., et al., "Frequency-Independent Equivalent-Circuit Model for On-Chip Spiral Inductors," IEEE Journal of Solid-State Circuits, Mar. 2003, vol. 38, No. 3, pp. 419-426.

Cao, C., et al., "Millimeter-Wave Voltage-Controlled Oscillators in 0.13-pm CMOS Technology," IEEE Journal of Solid-State Circuits, Jun. 2006, vol. 41, No. 6, pp. 1297-1304.

Chuang, H.R., et al., "60-GHz Millimeter-Wave Life Detection System (MLDS) for Noncontact Human Vital-Sign Monitoring," IEEE Sensors Journal, Mar. 2012, vol. 12, No. 3, pp. 602-609.

Dickson, T.O., et al., "30-100-GHz Inductors and Transformers for Millimeter-Wave (Bi)CMOS Integrated Circuits," IEEE Transactions on Microwave Theory and Techniques, Jan. 2005, vol. 53, No. 1, pp. 123-133.

Jentzsch, A., et al., "Theory and Measurements of Flip-Chip Interconnects for Frequencies up to 100 GHz," IEEE Transactions on Microwave Theory and Techniques, May 2001, vol. 49, No. 5, pp. 871-878.

Kao, T.Y., et al., "Design and Analysis of a 60-GHz CMOS Doppler Micro-radar Systemin-Package for Vital Sign and Vibration Detection," IEEE Transactions on Microwave Theory and Techniques, Mar. 2013, vol. 61, No. 4, pp. 1649-1659.

Kao, T.Y., et al., "A Flip-Chip-Packaged and Fully Integrated 60 GHz CMOS Micro-Radar Sensor for Heartbeat and Mechanical Vibration Detections," IEEE Radio Frequency Integrated Circuits Symposium, Jun. 2012, pp. 443-446.

Kraemer, M., et al., "Accurate Electromagnetic Simulation and Measurement of Millimeter-wave Inductors in Bulk CMOS Technology," Proceedings of the 1dh Topical Meeting on Silicon Monolithic Integrated Circuits in RF Systems, Jan. 2010, pp. 61-64.

Kuo, J.L., et al., "A 50 to 70 GHz Power Amplifier Using 90 nm CMOS Technology," IEEE Microwave and Wireless Components Letters, Jan. 2009, vol. 19, No. 1, pp. 45-47.

Laskin, E., et al., "Nanoscale CMOS Transceiver Design in the 90-170-GHz Range," IEEE Transactions on Microwave Theory and Techniques, Dec. 2009, vol. 57, No. 12, pp. 3477-3490.

Lee, J., et al., "A Low-Power Low-Cost Fully-Integrated 60-GHz Transceiver System With OOK Modulation and On-Board Antenna Assembly," IEEE Journal of Solid-State Circuits, Feb. 2010, vol. 45, No. 2, pp. 264-275.

Li, C., et al., "High-Sensitivity Software-Configurable 5.8 GHz Radar Sensor Receiver Chip in 0.13 µm CMOS for Non contact Vital Sign Detection," IEEE Transactions on Microwave Theory and Techniques, May 2010, vol. 58, No. 5, pp. 1410-1419.

Liang, C.K., et al., "Systematic Transistor and Inductor Modeling for Millimeter-Wave Design," IEEE Journal of Solid-State Circuits, Feb. 2009, vol. 44, No. 2, pp. 450-457.

Lu, H. C., et al., "Flip-Chip-Assembled W-Band CMOS Chip Modules on Ceramic Integrated Passive Device With Transition Compensation for Millimeter-Wave System-in-Package Integration," IEEE Transactions on Microwave Theory and Techniques, Mar. 2012, vol. 60, No. 3, pp. 766-777.

Pellerano, S., et al., "A 64 GHz LNA With 15.5 dB Gain and 6.5 dB NF in 90 nm CMOS," IEEE Journal of Solid-State Circuits, Jul. 2008, vol. 43, No. 7, pp. 1542-1552.

(56) References Cited

OTHER PUBLICATIONS

Petkie, D.T., et al., "Millimeter Wave Radar for Remote Measurement of Vital Signs," IEEE Radar Conference, May 2009, pp. 1-3.
Reynolds, S.K., et al., "A Silicon 60-GHz Receiver and Transmitter Chipset for Broadband Communications," IEEE Journal of Solid-State Circuits, Dec. 2006, vol. 41, No. 12, pp. 2820-2831.
Yan, W.S.T., et al., "A 900-MHz CMOS Low-Phase-Noise Voltage-Controlled Ring Oscillator," IEEE Transactions on Circuits and Systems II: Analog and Digital Signal Processing, Feb. 2001, vol. 48, No. 2, pp. 216-221.
Yao, T., et al., "Algorithmic Design of CMOS LNAs and PAs for 60-GHz Radio," IEEE Journal of Solid-State Circuits, May 2007, vol. 42, No. 5, pp. 1044-1057.
Benotsch, E.G., et al. "Rapid Anxiety Assessment in Medical Patients: Evidence for the Validity of Verbal Anxiety Readings," Annals of Behavioral Medicine, 2000, vol. 22, No. 3, pp. 199-203.
Camacho, A., "SWIPE: A Sawtooth Waveform Inspired Pitch Estimator for Speech and Music," Doctoral dissertation, University of Florida, 2007.
Froming, K.B., et al., "Comprehensive Affect Testing System (CATS)", 2006, http://www.psychologysoftware.com/CATS.htm.
Geisheimer, J., et al., "A Non-Contact Lie Detector Using Radar Vital Signs Monitor (RVSM) Technology," IEEE Aerospace and Electronic Systems Magazine, Aug. 2001, vol. 16, No. 8, pp. 10-14.
Gobl, C., et al., "The Role of Voice Quality in Communicating Emotion, Mood and Attitude," Speech Communication, Apr. 2003, vol. 40, Nos. 1-2, pp. 189-212.
Hillenbrand, J., et al., "Acoustic Correlates of Breathy Vocal Quality: Dysphonic Voices and Continuous Speech," Journal of Speech and Hearing Research, Apr. 1996, vol. 39, No. 2, pp. 311-321.
Patel, S., "Acoustic Correlates of Emotions Perceived from Suprasegmental Cues in Speech," Doctoral dissertation, University of Florida, 2009.
Scherer, K.R., "Vocal Affect Expression: a Review and a Model for Future Research," Psychological Bulletin, Mar. 1986, vol. 99, No. 2, pp. 143-165.
Schroder, M., "Experimental Study of Affect Bursts," Speech Communication, Apr. 2003, vol. 40, Nos. 1-2, pp. 39-116.
Venkatesh, S., et al., "Implementation and Analysis of Respiration-Rate Estimation Using Impulse-Based UWB," IEEE Military Communications Conference, Oct. 17-20, 2005, vol. 5, pp. 3314-3320.
Westbrook, R.A., et al., "The Dimensionality of Consumption Emotion Patterns and Consumer Satisfaction," Journal of Consumer Research, Jun. 1991, vol. 18, No. 1, pp. 84-91.
Xiao, Y., et al., "A Portable Noncontact Heartbeat and Respiration Monitoring System Using 5-GHz Radar", IEEE Sensors Journal, pp. 1042-1043, Jul. 2007, vol. 7, No. 7.
Li, C., et al., "Robust Overnight Monitoring of Human Vital Signs by a Non-Contact Respiration and Heartbeat Detector", 28th IEEE EMBS Annual International Conf., pp. 2235-2238, 2006.
Xiao, Y., et al., "Frequency-Tuning Technique for Remote Detection of Heartbeat and Respiration Using Low-Power Double-Sideband Transmission in the Ka-Band", IEEE Trans. on Microwave Theory and Techniques, pp. 2023-2032, May 2006, vol. 54, No. 5.
Chen, K., et al., "Microwave Life Detection Systems for Searching Human Subjects Under Earthquake Rubble or Behind Barrier", IEEE Trans on Biomedical Eng., p. 105-114, Jan. 2000, vol. 27, No. 1.
Abramov et al., English Abstract RU 2295911, Mar. 2007.
Li, C. et al., "Complex Signal Demodulation and Random Body Movement Cancellation Techniques for Non-Contact Vital Sign Detection", Microwave Symposium Digest, IEEE MTT-S International, Jun. 2008, pp. 567-570.
Park, B. et al., "Arctangent Demodulation with DC Offset Compensation in Quadrature Doppler Radar Receiver Systems", IEEE Trans. Microwave Theory and Techniques, May 2007, pp. 1073-1079, vol. 55, No. 5.
Li, C. et al., "Design Guidelines for Radio Frequency Non-Contact Vital Sign Detection," Proceedings of the 291th Annual International Conference of the IEEE EMBS, Aug. 2007, pp. 1651-1654.
Li, C. et al., "Optimal Carrier Frequency of Non-Contact Vital Sign Detectors," Proceedings of IEEE Radio and Wireless Symposium, Jan. 2007, pp. 281-284.
Droitcour, A.D. et al., "Range Correlation and I/Q Performance Benefits in Single-Chip Silicon Doppler Radars for Non-Contact Cardiopulmonary Monitoring," IEEE Trans. Microwave Theory and Techniques, Mar. 2004,pp. 838-848, vol. 52, No. 3.
Budge, Jr., M.C. et al., "Range Correlation Effects on Phase and Amplitude Noise", Proc. IEEE Southeast Conf., 1993, pp. 5-9.
Droitcour, A.D., "Non-Contact Measurement of Heart and Respiration Rates with a Single Chip Microwave Doppler Radar," Stanford University, Jun. 2006.
Li, C. et al., "Experiment and Spectral Analysis of a Low-Power Ka-Band Heartbeat Detector Measuring From Four Sides of a Human Body,"IEEE Transactions on Microwave Theory and Techniques, Dec. 2006, pp. 4464-4471, vol. 54, No. 12.
Li, C. et al., "Random Body Movement Cancellation in Doppler Radar Vital Sign Detection," IEEE Transactions on Microwave Theory and Techniques, Dec. 2008, pp. 3143-3152, vol. 56, No. 12.
Xiao, Y. et al., "A Ka-Band Low Power Doppler Radar System for Remote Detection of Cardiopulmonary Motion", Proceedings of the 2005 IEEE Engineering in Medicine and Biology 27th Annual Conference, Sep. 2005, pp. 7151-7154.
Samardzija et al., "Applications of MIMO techniques to Sensing Cardiopulmonary Activity", 2005, pp. 1-4.
Xiao, Y., et al., "Accuracy of a Low-Power Ka-Band Non-Contact Heartbeat Detector Measured from Four Sides of a Human Body," Department of Electrical & Computer Engineering, 2006, pp. 1576-1579.
Pan et al., "A real-time QRS detection algorithm," IEEE Trans. Biomed. Eng., Mar. 1985, vol. 32, No. 3, pp. 230-236.
Razavi, B., "Design Considerations for Direct-Conversion Receivers," IEEE Trans. on Circuits and Systems II: Analog and Digital Signal Processing, Jun. 1997, vol. 44, No. 6, pp. 428-435.
Gu et al., "Instrument-based noncontact Doppler radar vital sign detection system using heterodyne digital quadrature demodulation architecture," IEEE Trans. Instrum. Meas., Jun. 2010, vol. 59, No. 6, pp. 1580-1588.
Lin, James C. "Noninvasive microwave measurement of respiration." Proceedings of the IEEE 63.10 (Oct. 1975): 1530-1530.
Yavari, Ehsan, and Olga Boric-Lubecke. "Low IF demodulation for physiological pulse Doppler radar." Microwave Symposium (IMS), 2014 IEEE MTT-S International. IEEE, (Jun. 2014).
Gu, Changzhan, et al. "Instrument-based noncontact Doppler radar vital sign detection system using heterodyne digital quadrature demodulation architecture." IEEE Transactions on Instrumentation and Measurement 59.6 (Jun. 2010): 1580-1588.
Mostafanezhad, Isar, and Olga Boric-Lubecke. "Benefits of coherent low-IF for vital signs monitoring using Doppler radar." IEEE Transactions on Microwave Theory and Techniques 62.10 (Oct. 2014): 2481-2487.
Ramachandran, G., and M. Singh. "Three-dimensional reconstruction of cardiac displacement patterns on the chest wall during the P, QRS and T-segments of the ECG by laser speckle inteferometry." Medical and Biological Engineering and Computing 27.5 (Sep. 1989): 525-530.
Singh, Megha, and G. Ramachandran. "Reconstruction of sequential cardiac in-plane displacement patterns on the chest wall by laser speckle interferometry." IEEE transactions on biomedical engineering 38.5 (May 1991): 483-489.
International Search Report for PCT/US2015/054669 dated Dec. 29, 2015.
Lin, "Microwave Doppler Radar Sensor for Detection of Human Vital Signs and Mechanical Vibrations", Feb. 10, 2012. [retrieved on Nov. 19, 2015]. Retrieved from the Internet. <URL: http:l/abe.ufl.edu/research/CRS/seminar/20120210_Lin_Seminar.pdf>.

* cited by examiner

TABLE I
ERROR IN HEART RATE MEASUREMENTS

| Heart rate Root Mean Square error (bpm) | Subject 1 (male) | Subject 2 (female) | Subject 3 (male) |
|---|---|---|---|
| data set 1 | 3.27 | 3.93 | 3.84 |
| data set 2 | 3.73 | 3.76 | 4.38 |

METHOD AND APPARATUS FOR NON-CONTACT FAST VITAL SIGN ACQUISITION BASED ON RADAR SIGNAL

CROSS REFERENCE TO RELATED APPLICATIONS

This application is a continuation application claiming priority to, and the benefit of, U.S. non-provisional application having Ser. No. 15/517,214, filed Apr. 6, 2017, which is the 35 U.S.C. § 371 national stage application of PCT Application No. PCT/US2015/054669, filed Oct. 8, 2015, where the PCT claims priority to, and the benefit of, U.S. provisional application entitled "METHOD AND APPARATUS FOR NON-CONTACT FAST VITAL SIGN ACQUISITION BASED ON RADAR SIGNAL" having Ser. No. 62/061,320, filed Oct. 8, 2014, both of which are herein incorporated by reference in their entireties.

BACKGROUND

Accurate determination of patient vital signs is important in many situations. Research results show that non-contact vital sign sensing has significant advantages in applications such as detecting human subjects in disaster in-field rescue, through-wall human tracking, apexcardiography (ACG) measurement for hemodynamics monitoring and evaluating the status of patients who are exposed to toxic chemicals or suffer serious burn wounds.

SUMMARY

Embodiments of the present disclosure are related to non-contact vital sign acquisition such as fast acquisition of vital signs based on radar signals. Embodiments can be used for providing information regarding vibrations of a target using a radar signal. Embodiments can be used for non-contact vital sign measurement using a radar signal. Various embodiments relate to a method and apparatus for heart rate estimation. Embodiments can also provide respiration rate. Embodiments can be used to provide heart rate, change in heart rate, respiration rate, and/or change in respiration rate for a human, an animal, a dog, a cat, a horse, or other animal. Embodiments can also be used to produce one or both rates of vibration and/or change in one or both rates of vibration for a target other than an animal or human that is experiencing two vibrations at the same time, such as a motor, a vehicle incorporating a motor, or another physical object.

Embodiments can estimate the respiration movement in the radar baseband output signal. The estimated respiration signal can then be subtracted from radar signals in time domain and, optionally, further enhanced using digital signal processing techniques, to produce an estimate of the heartbeat pulses. The use of time-domain subtraction can result in a vital sign extraction and estimation method having certain advantages compared with traditional vital sign estimation methods based on spectral analysis.

Embodiments can utilize a peak detection algorithm. By detecting respiration peaks and performing a polynomial fit according to the locations of the respiration peaks, the respiration signal (including the harmonic components of the respiration signal) can be filtered out from the radar baseband signal, and can achieve real time extraction of the heartbeat pulses. The heart rate and respiration rate can be calculated by estimating the time intervals between extracted peaks. Embodiments can realize a fast estimation of vital sign information.

Various embodiments can have one or more of the following advantages. Extraction of time-domain waveforms for respiration and heartbeats can reduce, or eliminate, a spectrum distortion problem (e.g., higher order harmonics of respiration overwhelming heartbeat signal) common in frequency-domain analysis. A real-time respiration and heartbeat waveform can be produced for fast vital sign estimation, such as within 20 seconds, 15 seconds, 10 seconds, 9 seconds, 8 seconds, 7 seconds, 6 seconds, and/or 5 seconds. Real time changes in the heart rate and/or real time changes in the respiration rate can be produced, which can be useful for some medical analyses, such as the Heart Rate Variability (HRV) analysis.

Some embodiments can suppress signals due to respiration, such as fundamental respiration signal and/or higher order harmonics of the fundamental respiration signal, and can extract heartbeat pulses using a real-time time-domain analysis, without harmonic distortion, to provide fast and accurate vital sign estimation. Embodiments can produce a time varying output of the respiration rate and/or time-varying output of the heart rate. Embodiments can output a signal reading of the respiration rate and/or heart rate, or produce an updated reading of the respiration rate and/or heart rate every X seconds, such as every 60 seconds, every 30 seconds, every 15 seconds, every 10 seconds, every 5 seconds, and/or some other period of time. Compared to previous spectral-domain methods that typically have a delay of more than 20 seconds, embodiments of the subject method and apparatus have less delay, and can produce a heart rate reading in less than 20 seconds, e.g., within 6 seconds, within 5 seconds, within 4 seconds, within 3 seconds, and/or within 2 seconds.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
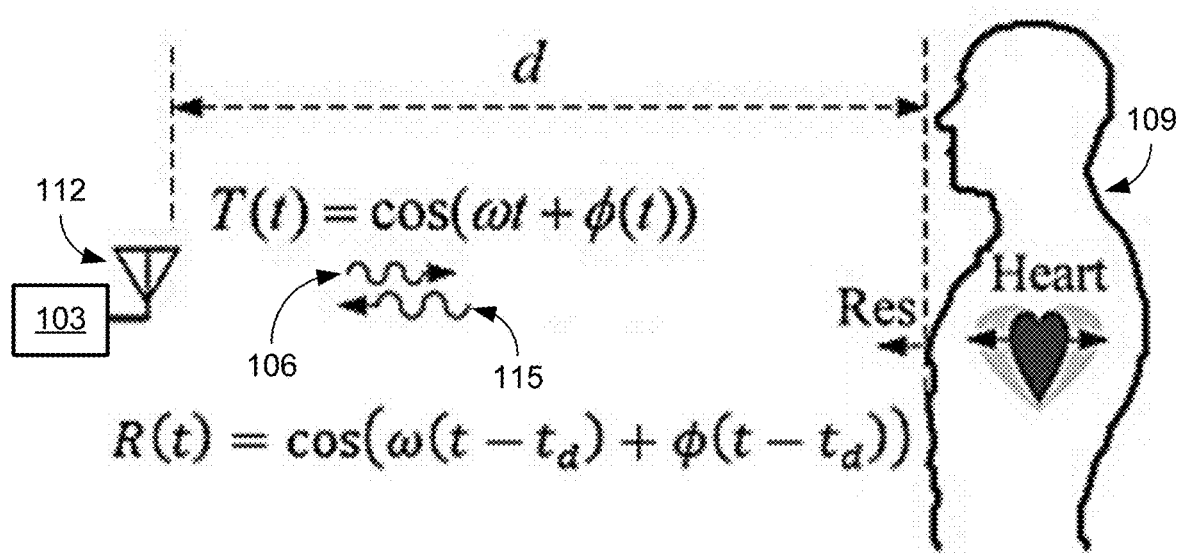
FIG. 1 illustrates an example of the operation of vital sign detection using Doppler vital sign radar, in accordance with various embodiments of the present disclosure.

Disclosed herein are various embodiments of methods, systems and apparatus related to non-contact vital sign acquisition. Fast acquisition of vital signs is possible based on radar signals. Reference will now be made in detail to the description of the embodiments as illustrated in the drawings, wherein like reference numbers indicate like parts throughout the several views.

Embodiments can be used for providing information regarding vibrations of a target using a radar signal. Embodiments can be used for non-contact vital sign measurement using a radar signal. Various embodiments relate to a method and apparatus for heart rate or other vital sign estimation. Embodiments can also provide respiration rate. Embodiments can be used to provide heart rate, change in heart rate, respiration rate, and/or change in respiration rate for a human, an animal, a dog, a cat, a horse, or other animal. Embodiments can also be used to produce one or both rates of vibration and/or change in one or both rates of vibration for a target other than an animal or human that is experiencing two vibrations at the same time, such as a motor, a vehicle incorporating a motor, or another physical object.

Embodiments can estimate the respiration movement in the radar baseband output signal. The estimated respiration signal can then be subtracted from radar signals in time domain and, optionally, further enhanced using digital signal processing techniques, to produce an estimate of the heartbeat pulses. The use of time-domain subtraction can result in a vital sign extraction and estimation method having certain advantages compared with traditional vital sign estimation methods based on spectral analysis.

One challenge in vital sign sensing is the estimation of a subject's heart rate from the reflected radar signals. While measuring from the front side of a person, the reflected radar signal can be dominated by respiration movements. The higher order harmonics of the respiration can overwhelm the heartbeat components, causing errors or inaccuracy in heart rate estimation. Reliable heart rate estimation from a reflected radar signal distorted by respiration movements may be achieved through various methods.

The heart rate may be measured from the back side of human subjects where the respiration movement is not significant. This method can be applied to subjects staying in bed with the right posture for measurements. Differential radiation, front end implemented with two antennas, can be used to estimate respiration movements. By canceling the respiration signal, the quality of heartbeat signal can be improved. However, respiration can also introduce differential signals in the dual antenna design and corrupt the heartbeat waveforms. Advanced signal processing methods, such as RELAX, may be used to improve the heart rate estimation in a limited measurement time window. However, such advanced signal processing methods utilize significant computational power and relatively long measurement periods for data analysis. For example, data having a 13.5 s length can be used for heart rate estimation. Such long measurement periods can cause undesirable delay in real time applications.

A heart rate estimation method is discussed in this disclosure, which can be based on peak detection. By detecting respiration peaks and conducting polynomial fit according to the peaks' locations, the respiration signal (which can include its harmonic components) can be filtered out from the radar baseband signal and achieve real time heartbeat pulses extraction. Since the heart rate and respiration rate can be calculated via estimating the time intervals between extracted peaks, this algorithm provide a fast estimation of vital sign information.

FIG. 1 illustrates an example of the principle of operation of a Doppler radar vital sign detection method and system in accordance with various embodiments of the present disclosure. As shown in the example of FIG. 1, a Doppler radar system 103 sends a transmitting signal 106, which can be expressed as:

$$T(t)=\cos(\omega t+\phi(t)), \quad (1)$$

toward the human subject 109, where φ(t) is the phase noise of the oscillator in the radar system 103. The radar signal 106 can have a frequency in the range from 1 GHz to 30 GHz, although other frequencies can be used. As examples, for small animals with smaller vital sign physiological displacements, the frequency range can be higher than 30 GHz, and for large animals with larger vital sign physiological displacements, the frequency range can be lower than 1 GHz.

In the example of FIG. 1, the transmitted signal 106 (e.g., at 5.8 GHz) hits the front chest of the subject 109 and is reflected back to the sensor 112 (e.g., an antenna) of the radar system 103. The reflected signal 115 received by the sensor 112 can be expressed as:

$$R(t)=\cos(\omega(t-t_d)+\phi(t-t_d)), \quad (2)$$

where $t_d$ is the time needed for the transmitted radar signal 106 to travel from the transmitting antenna to the subject and for the reflected signal 115 to travel from the subject 109 back to the receiving antenna 112.

Assuming the transmitting and receiving antennas 112 are the same distance, d, from the subject 109, then:

$$t_d=2d/c, \quad (3)$$

where c is the light speed in free space and d is the distance between the radar transmitting antenna 112 and the subject 109. The distance between the receiving antenna 112 and the subject 109 can also be assumed to be d if the transmitting and receiving antennas 112 are the same distance from the subject 109. In some embodiments, a single antenna 112 can be utilized to both transmit and receive and, in other embodiments, separate transmitting and receiving antennas can be used. When separate antennas are used, the distance from the transmitting antenna to the subject may be different than the distance from the receiving antenna to the subject.

If the transmitting antenna and receiving antenna are not the same distance from the subject, then equations (2) and (3) can be adjusted. When the distance, $d_t$, from the transmitting antenna to the subject 109 is approximately the same as the distance, $d_r$, from the subject 109 to the receiving antenna 112 and the time $t_d=(d_t+d_r)/c$, the approximation that $d_t=d_r=d$ produces satisfactory results.

The distance, d, can be expanded as:

$$d=d_0+x_h(t)+x_r(t), \quad (4)$$

where $x_h(t)$, $x_r(t)$ are the movements of the subject's front chest due to heartbeat and respiration, and $d_0$ is the averaged distance between the radar 103 and the subject 109. In short distance measurements (for example, where $d_0$ is 1 m or less), the phase noise of the oscillator can be approximated as $\phi(t-t_d) \approx \phi(t)$ due to the range correlation effects.

As an example, the received radar signal 115 can then be approximated as $\phi(t-t_d) \approx \phi(t)$ when d (the distance between transmitting antenna and target) is less than 300 m, and the roundtrip delay, $t_d$ when the transmitting antenna and receiving antenna are the same distance from the subject is less than 2 µs (microseconds). This delay is sufficiently short that the random phase fluctuations (or phase noise) of the signal source with rates near the vital sign rates is greatly reduced by self-mixing at the radar receiver (the so-called range correlation effect).

The reflected signal 115 received by the receiver can then be approximated by:

$$R(t) \approx I(t)\cos(\omega t+\phi t))+Q(t)\sin(\omega t+\phi(t)), \quad (5)$$

where $I(t)$ is the I channel, $I(t)=\cos(4\pi d/\lambda)$ and Q(t) is the Q channel, $Q(t)=\sin(4\pi d/\lambda.)$. A signal representative of the received radar signal 115 can then be produced, and analyzed to obtain information about the vibrations of the target 109. Examples of a signal representative of the received radar signal 115 include, but are not limited to, the I channel, the Q channel, the better signal of the I channel and the Q channel, or some combination of the I channel and Q channel such as aI+bQ or aI+ibQ, where a and b are constants. The signal representative of the received radar signa R(t)I can then be processed to extract information regarding one or more vibrations, e.g., the vibrations of respiration and/or heartbeat.

In a specific embodiment, the signal representative of R(t) is the baseband signal B(t). By combining 1(t) and Q(t) signals, the baseband signal B(t), whose phase contains the vital sign information, can be represented as:

$$B(t)=I(t)+jQ(t)=\exp(j4\pi d_0/\lambda)\exp(j(4\pi x_h(t)+4\pi x_r(t))/\lambda). \quad (6)$$

Figure 2:
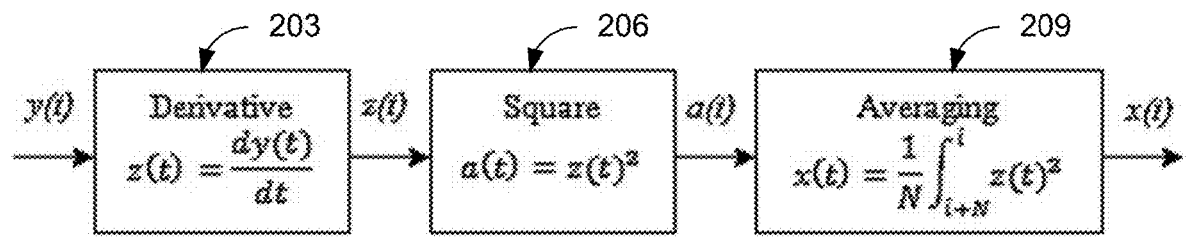
FIG. 2 is a flow chart illustrating an example of Tompkins peak detection and enhancement, in accordance with various embodiments of the present disclosure.

A subject's vital sign information can be estimated by analyzing the baseband signal B(t), which is representative of the received signal 115. B(t) can be analyzed within a short time window, such as within 20, 15, 10, 9, 8, 7, 6, 5, 4, 3, 2, and/or 1 seconds. Elements of a peak enhancement and detection algorithm for QRS peaks identification in ECG waveforms can be included. Referring to FIG. 2, shown is a flow chart illustrating an example of the application of elements of a peak enhancement and detection algorithm that can be utilized in accordance with various embodiments of this disclosure.

Signal y(t) is first passed through a digital differentiator to apply a derivative operation 203. This step can help sharpen the peaks in y(t). The resulting signal z(t) then goes through processing circuitry that can apply a squaring operation 206 and an averaging operation 209 to reform peaks in the output signal x(t). The extracted peaks in x(t) can then be located. For example, the extracted peaks in x(t) can be located by an adaptive thresholding method such as that discussed in "A real-time QRS detection algorithm" by Pan et al. (*IEEE Trans. Biomed. Eng.*, vol. 32, no. 3, pp. 230-6, March 1985), which is hereby incorporated by reference in its entirety. Alternative embodiments can utilize the derivative operation 203 and the squaring operation 206, without the averaging operation 209; utilize the squaring operation 206 and the averaging operation 209, without using the derivative operation 203; or use the derivative operation 203 and averaging operation 209, without using the squaring operation 206.

Figure 3:
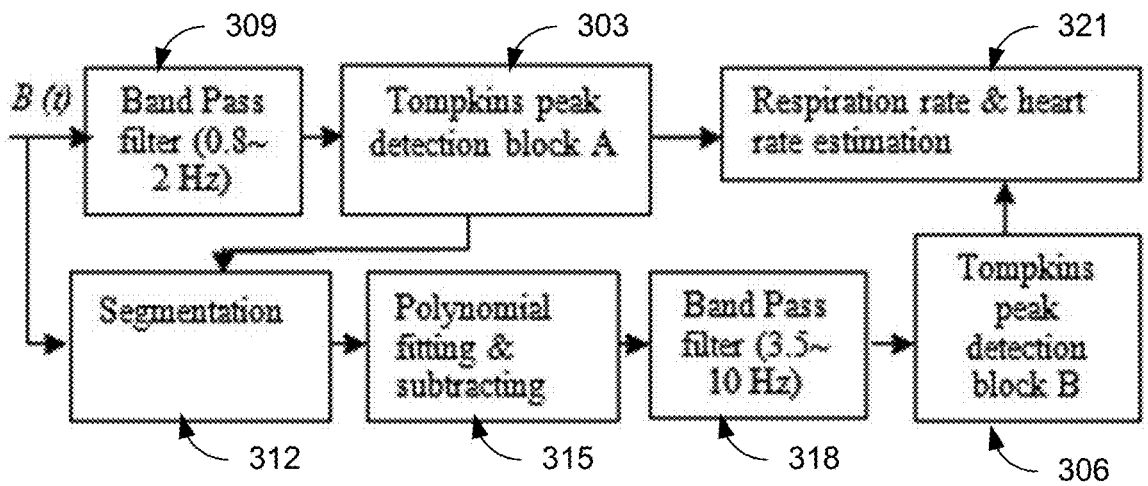
FIG. 3 is a block diagram illustrating an example of fast vital sign detection, in accordance with various embodiments of the present disclosure.

Referring now to FIG. 3, shown is a block diagram illustrating an example of vital sign estimation in accordance with a various embodiments of the present disclosure. In the example of FIG. 3, two Tompkins peak detection blocks (block A and block B) 303 and 306 are implemented separately for detecting respiration peaks and heartbeat peaks. Other embodiments can utilize block A 303 and not block B 306, or utilize block B 306 and not block A 303. As shown in FIG. 3, by first band pass filtering 309 (e.g., a 0.8-2 Hz passband) the baseband radar signal B(t) to depress the low frequency DC drift and high frequency noise, the signal-to-noise ratio of the respiration harmonics within B(t) can be enhanced, which can improve respiration peaks detection. Other embodiments can use a different band for the band pass filter 309, apply a high pass filter (e.g., greater than 0.8 Hz), apply a low pass filter (e.g., less than 2 Hz), apply a combination of filters (e.g., high, low, and/or band pass filters), or apply no filtering. The Tompkins block A 303 in FIG. 3 is used to locate the respiration peaks with the adaptive thresholding method. The located respiration peaks can then be used to separate the baseband signal B(t) into segments (segmentation 312) for polynomial fitting and subtraction 315. After the subtraction of the respiration signal at 315, the remaining signal, which contains the heartbeat pulses, can be passed through another band pass filter 318 (e.g., a 3.5-10 Hz passband) to enhance the signal noise ratio of the heartbeat. Again, other embodiments can use alternative filtering as discussed above or no filtering. The remaining signal containing the heartbeat pulses can then be processed by the Tompkins peak detection block B 306 shown in FIG. 3 for heartbeat peaks detection. The extracted respiration and heartbeat peaks are sent from the Tompkins peak detection blocks (block A and block B) 303 and 306 to the sequential block for respiration and heart rates estimation 321.

Figure 4:
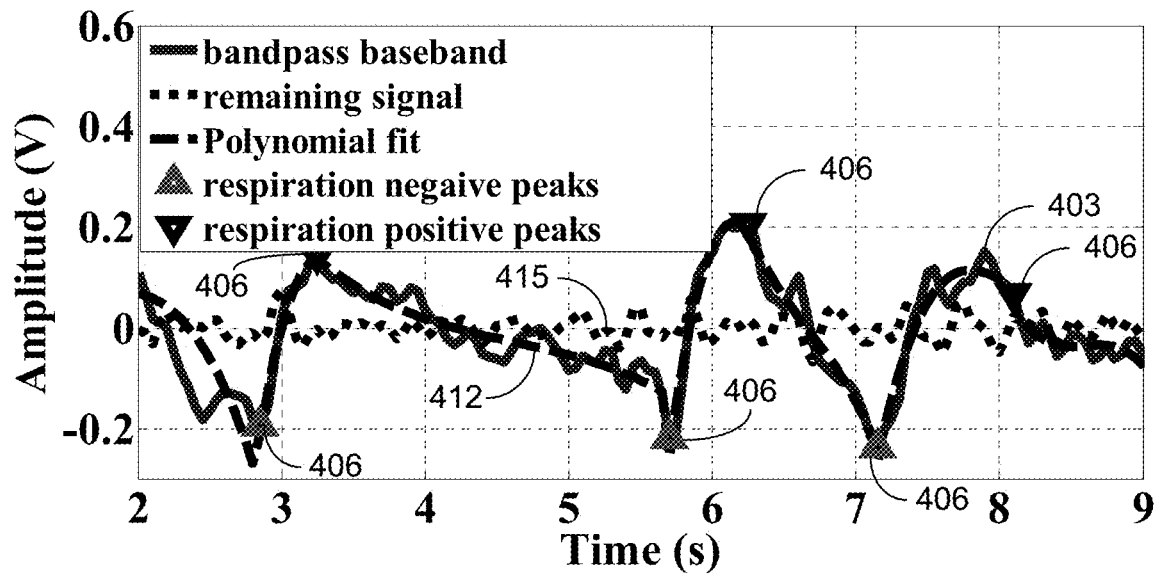
FIG. 4 illustrates examples of bandpass signal amplitude versus time, polynomial fit of the respiration signal, remaining signal, and respiration negative and positive peaks, in accordance with various embodiments of the present disclosure.

Referring now to FIG. 4, shown is the result of respiration peaks detection and polynomial fit on the baseband signal B(t) 403, where the distance between the radar 103 (FIG. 1) and the subject 109 (FIG. 1) is 1 meter during the measurement. The Tompkins block A 303 (FIG. 3) locates the positive peaks 406 and negative peaks 409 in the respiration movements. By estimating the time intervals between the positive peaks 406, the respiration rate can be estimated 321 (FIG. 3). In some embodiments, the respiration rate can be estimated 321 in a variety of manners such as, but not limited to: estimating the time interval between a positive peak 406 and a negative peak 409; estimating the time intervals between the negative peaks 409; averaging the estimate of time intervals between positive peaks 406 and the estimate of time intervals between negative peaks 409; averaging the estimates of time intervals between positive peaks 406 over a certain number of adjacent positive peaks 406; averaging the estimates of time intervals between negative peaks 409 over a certain number of negative peaks 409; or other manners of combining the information regarding the location of the positive peaks 406 and/or negative peaks 409.

In one embodiment, among others, the band pass baseband signal B(t) 403 is separated into segments 312 (FIG. 3) using the located respiration peaks. The signal between consecutive respiration peaks (either positive peaks 406 or negative peaks 409) can be regarded as a segment and fitted 315 (FIG. 3) by a third degree polynomial under a Least Mean Square (LMS) standard. The resulting polynomial fit data 412 can then be subtracted 315 from the baseband signal B(t) 403, to create a remaining signal 415 comprising the heartbeat pulses and noise. Other degree polynomial fits (other than a third degree polynomial fit) can also be used, as can other curve fitting techniques.

Other techniques can be used to determine an approximation of the first vibration, which is to be subtracted 315 (FIG. 3) from the signal representative of the reflected signal R(t), such as B(t) 403, to produce the remaining signal 415. Such techniques to determine an approximation of the first vibration include, but are not limited to, measuring the respiration signal (as the first vibration) via video, via another radar signal, with the same or different wavelength, or by sending a radar signal at markers on the target. In the example of FIG. 3, the remaining signal 415 can then be processed by another band pass filter 318. The passband of the filter 318 can be experimentally set. In the example of FIG. 3, the passband filter 318 is set as 3.5-10 Hz, however other passbands can be used. For instance, the passband filter can be set so as to maximize the signal-to-noise ratio for heartbeat detection. The filtered signal can then be sent to Tompkins block B 306 for heartbeat peaks extraction and detection.

Figure 5A:
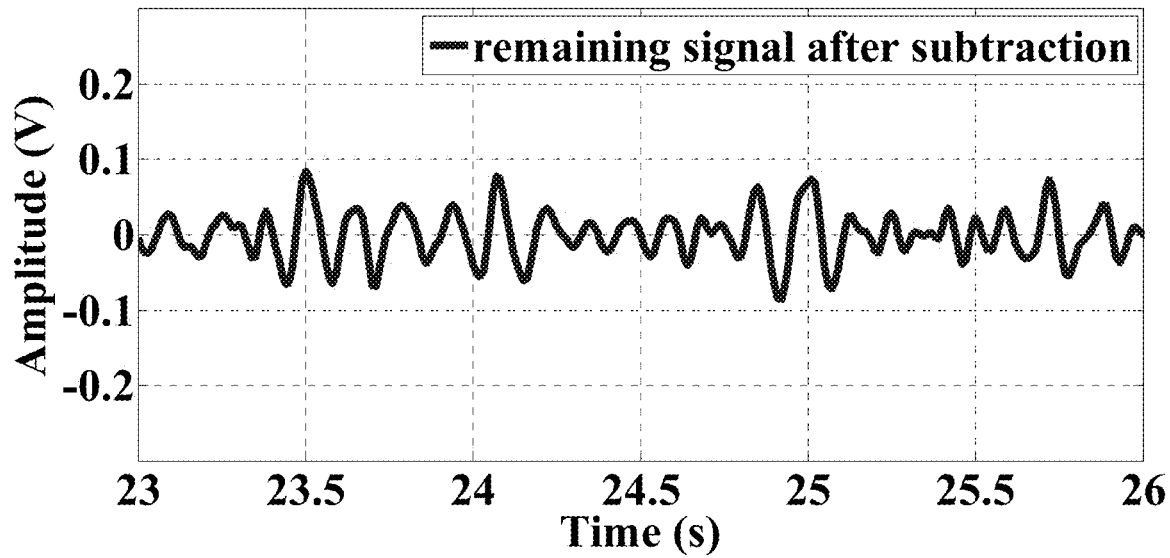
FIGS. 5A through 5C illustrates examples of signals after respiration movement subtraction and bandpass filtering, after taking the derivative and squaring, and after averaging, in accordance with various embodiments of the present disclosure.
Figure 5B:
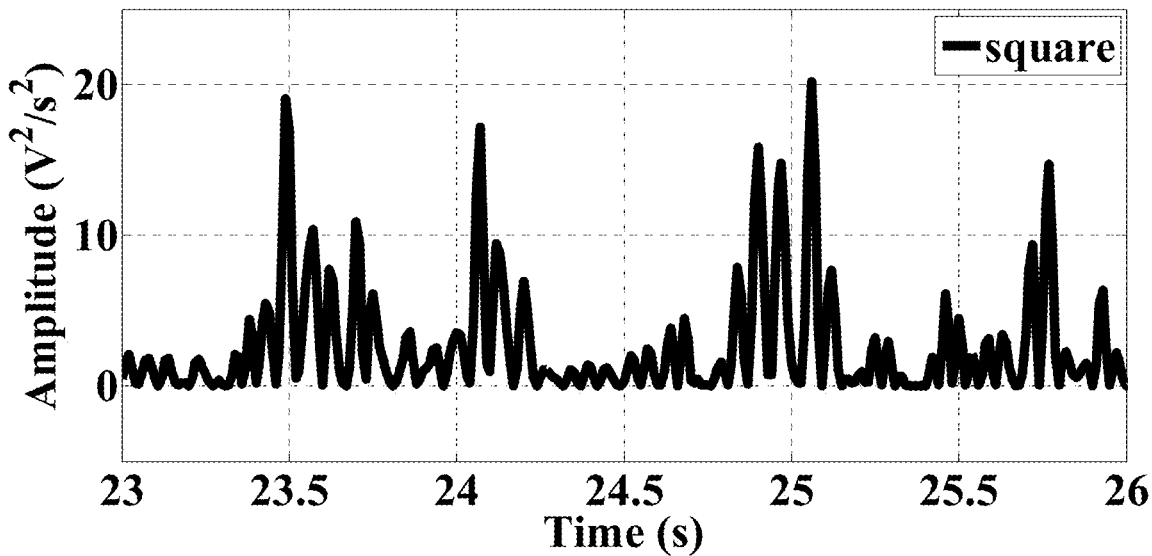
Figure 5C:
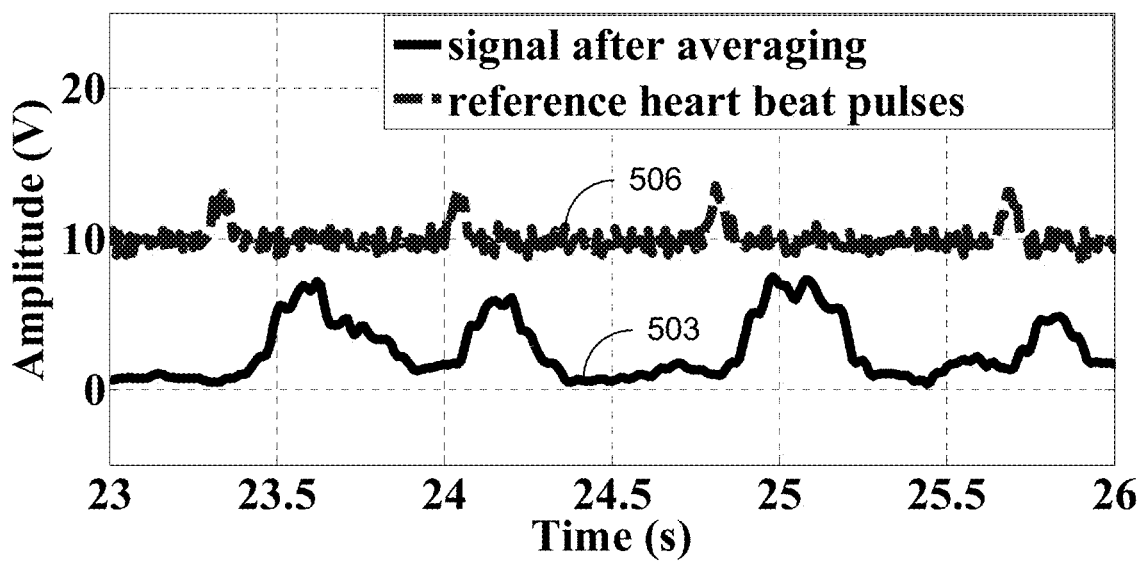

FIGS. 5A-5C show examples of how the heartbeat peaks can be extracted from the remaining baseband signal by applying the Tompkins peak detection. FIG. 5A shows the remaining signal after respiration movement subtraction 315 (FIG. 3) and band pass filtering 318 (FIG. 3). As shown in FIG. 5A, the heartbeat signal level is low and the heartbeat pulses are not obvious in the remaining band passed signal. In some embodiments, a derivative operation 203 (FIG. 2) can be applied to the remaining band passed signal, such as the remaining band passed signal shown in FIG. 5A. The signal remaining after the derivative operation 203 can then be operated on to take an absolute value or square, cube, or raise the signal by a larger exponent, or other operation, to enhance the difference between positive absolute values and zero.

FIG. 5B shows the result of an embodiment after a derivative operation 203 and a squaring operation 206 is applied. The remaining signal after the squaring operation 206, or other operation, can then be processed to extract the heartbeat pulses, or the time interval between adjacent heartbeat pulses. Such processing can count the number of local maxima's per a certain length of time and divide the length of time by the count to arrive at an averaging time period between heart beat pulses, which can be used to determine the heart rate. In some embodiments, averaging 209 (FIG. 2) can be applied.

Referring now to FIG. 5C, shown is a comparison between the signal 503 after the averaging operation 209 (FIG. 2) and the reference heartbeat pulses 506 from a contact sensor. The heartbeat pulses can be highlighted from the background noise. This can be confirmed by comparing the extracted heartbeat pulses 503 to the reference heartbeat pulses 506 also shown in FIG. 5C. The reference pulses 506 shown in FIG. 5C were recorded by a contact sensor (e.g., a piezoelectric pulse transducer) attached to the finger of the subject 109 (FIG. 1) during the experiment and are offset in FIG. 5C for the convenience of comparison. Similar to the estimation of the respiration rate, the heartbeat rate can be estimated by calculating the intervals between heartbeat peaks.

In one embodiment, the heart rate can be estimated by estimating the time intervals between the positive peaks. In alternative embodiments, the heart rate can be estimated in a variety of manners, such as, but not limited to: estimating the time interval between a positive peak and a negative peak; estimating the time intervals between the negative peaks; averaging the estimate of time intervals between positive peaks and the estimate of time intervals between negative peaks; averaging the estimates of time intervals between positive peaks over a certain number of adjacent positive peaks; averaging the estimates of time intervals between negative peaks over a certain number of negative peaks; or other manners of combining the information regarding the location of the positive and/or negative peaks.

Figures 6, 7:
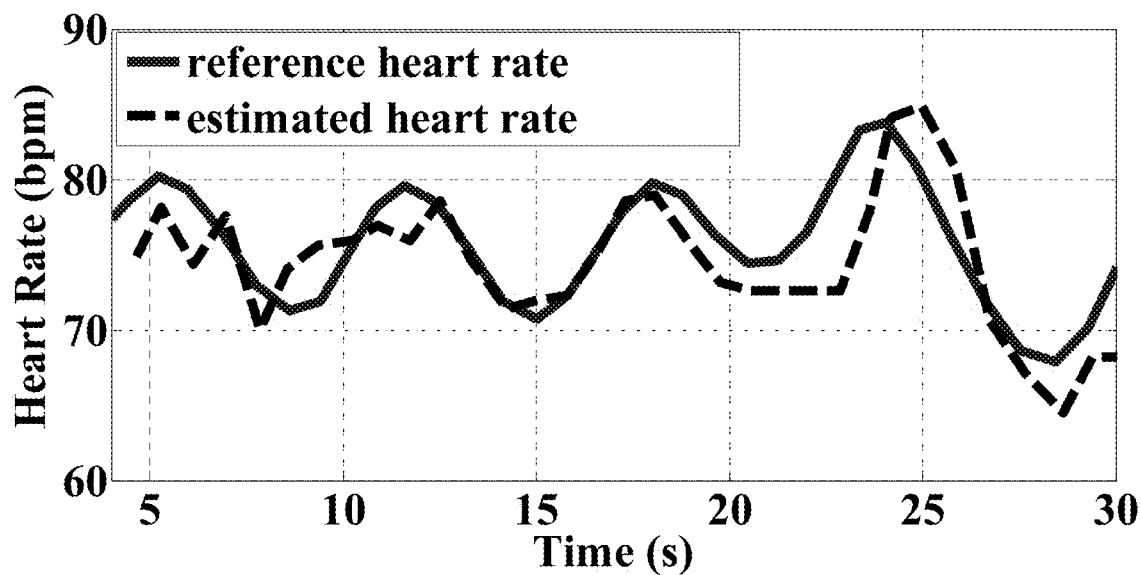
FIG. 6 illustrates an example of the estimated heart rate and the reference heart rate, in accordance with various embodiments of the present disclosure.
FIG. 7 is a table illustrating examples of error in heart rate measurements, in accordance with various embodiments of the present disclosure.

Referring next to FIG. 6, shown is a comparison between the real time heart rate 603, which was estimated using the vital sign extraction and estimation described above, and the reference heart rate 606 that was monitored using the contact fingertip sensor that produced the reference heart beat signal shown in FIG. 5C. From FIG. 6 it can be seen that, in a 30 second measurement period, the vital sign acquisition provides a first heart rate estimation 603 within 5 seconds (using 4 consecutive heartbeat pulses with similar amplitude), which is much faster than previously reported methods (e.g., using the RELAX algorithm). Other embodiments can use more than 4 consecutive heart beat pulses and achieve a greater accuracy, or use less than 4, such as 3 or 2 consecutive heart beat pulses, and produce a heart rate estimation in a shorter time. The estimation of heart rate shown in FIG. 6 appears to accurately track with the reference data.

Experiments with three subjects (two adult males and one adult female) were conducted to verify the performance of the vital sign acquisition. Each measurement was at least 40 seconds long and multiple measurements are taken on each subject. Table I in FIG. 7 illustrates the statistics of Root Mean Square (RMS) error of the measurements. The results show that the vital sign acquisition can provide fairly accurate estimates of heart rate, such that the RMS error was less than 5 bpm for the three subjects. From FIG. 6 it can be seen that, by evaluating the heart rate from heartbeat intervals, the vital sign acquisition is able to provide the subject's short-term heart rate variation.

Fast vital sign acquisition based on Tompkins peak detection and segmented polynomial fitting strategy has been presented. By fitting and subtracting respiration movements from radar baseband signal and conducting peaks enhancing and detection processing, real time heartbeat pulse extraction can be achieved from radar signals. By estimating the intervals of respiration peaks and heartbeat peaks, the analysis is able to provide a fast estimation of a subject's vital sign information. Although embodiments are taught using a third degree polynomial fit, a polynomial fit other than a third degree polynomial fit can be used. Further, embodiments can utilize other curve fit(s).

Next, a portable Doppler radar system for fast vital sign acquisition is presented. The hardware platform of the system can use a coupler to separate the transmitting and receiving (TX/RX) radar signals from the same antenna. This implementation can help to reduce the hardware size. The system can also feature an automatic gain control baseband amplifier for making measurements under different distances. The fast acquisition algorithm can be designed to shorten the sensor's measuring time. The algorithm can depress the respiration signal with polynomial fitting and extract the heartbeat pulses in time domain. An accurate estimation of subjects' physiology information can be achieved within a short measurement window by detecting the peaks of the processed respiration and heartbeat signals. The vital sign sensor can use a wireless communication module for transmitting measurement data. It can be packaged into a 60 mm×35 mm×30 mm box and powered by batteries to achieve great mobility.

Figure 8:
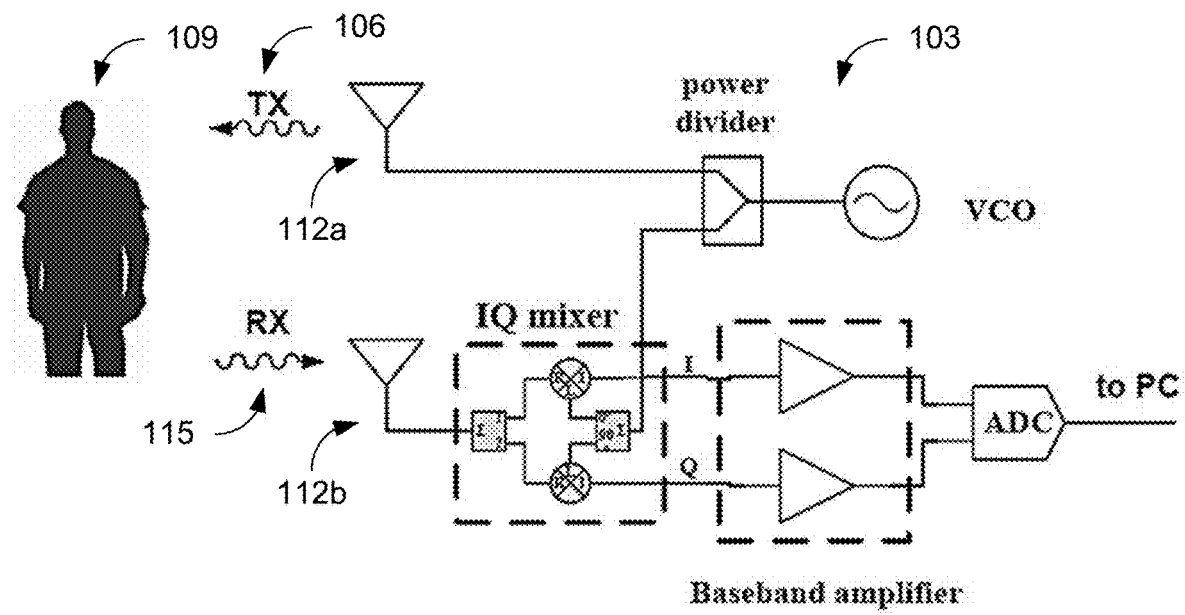
FIG. 8 is a schematic diagram illustrating an example of a radar system for non-contact vital sign detection, in accordance with various embodiments of the present disclosure.

The bulky, heavy, and expensive waveguide components used to implement radar sensors can limit their use to research environments. For applications such as battlefield first aid, earthquake rescue, and in-home health monitoring, various constraints should be considered to make a vital sign radar sensor serve better for the application scenarios. For the hardware aspect, the sensor system should be compact to make it easy to carry and deploy. It is also desirable for the system to adapt to the environmental changes and provide good measurement results under different measuring ranges. The algorithm for measurements should be able to estimate the subjects' physiology information within a short time, allowing the fast response sensor to save time in applications like disaster rescue and surveillance. A sensor that can provide a quick reading is also more user-friendly for healthcare monitoring. Besides, the vital sign acquisition should be able to separate the heartbeat signal effectively from the respiration signal, or other signals, to provide accurate heart rate estimation Referring to FIG. 8, shown is an example of a continuous wave (CW) Doppler radar 103 for non-contact vital sign detection. The CW Doppler radar 103 can send out a single tone sinusoidal transmission signal T(t) of equation (1) via the transmitting (TX) antenna 112a, which can be given by:

$$T(t)=A_t \cos(\omega t+\phi(t)), \qquad (7)$$

where $\phi(t)$ is the phase noise of the voltage controlled oscillator (VCO) of the radar system 103 and $A_t$ is the amplitude of the transmitted waveform. The signal T(t) hits the front chest of the subject 109 and is reflected back to the radar sensor 112b.

The backscattered signal R(t) of equation (2) is received by the radar sensor 112b, and can be represented as:

$$R(t)=A_r \cos(\omega(t-t_d)+\phi(t-t_d)+\theta), \qquad (8)$$

where $\theta$ is phase change due to the reflection and $t_d$ is the time delay introduced by the transmission of radar signal as given by equation (3). The distance, d, between the radar 103 and the subject 109 can be represented by equation (4). The backscattered signal R(t) can be rewritten in the following form:

$$R(t)=I(t)\cos(\omega t+\phi(t))+Q(t)\sin(\omega t+\phi(t)), \qquad (9)$$

where $$I(t) = A_I \cos\left(\frac{4\pi d}{\lambda} - \Delta\phi - \theta\right), \qquad (10)$$

$$Q(t) = A_Q \sin\left(\frac{4\pi d}{\lambda} - \Delta\phi - \theta\right), \qquad (11)$$

and $\Delta\phi=\phi(t-t_d)-\phi(t)$ is the difference of phase noise from the VCO. For short distance measurements (e.g., d<2 m), the phase noise of the oscillator is highly correlated in time and can be approximated as a low frequent signal. Thus, $\Delta\phi=\phi(t-t_d)-\phi(t)\approx 0$. Ignoring the demodulation imbalance, $A_I \approx A_Q = A_B$. By demodulating R(t) with the same VCO used for transmission, the signals I(t) and Q(t) can be retrieved. The baseband signal B(t) can be attained by combining I(t) and Q(t) such that:

$$B(t) = I(t) + jQ(t) = A_B \exp\left(j\left(\frac{4\pi d_0}{\lambda} - \theta\right)\right) \exp(j(4\pi x_h(t) + 4\pi x_r(t))/\lambda). \qquad (12)$$

The phase of B(t) contains the movements relating to the vital activities of the subjects.

Figure 9:
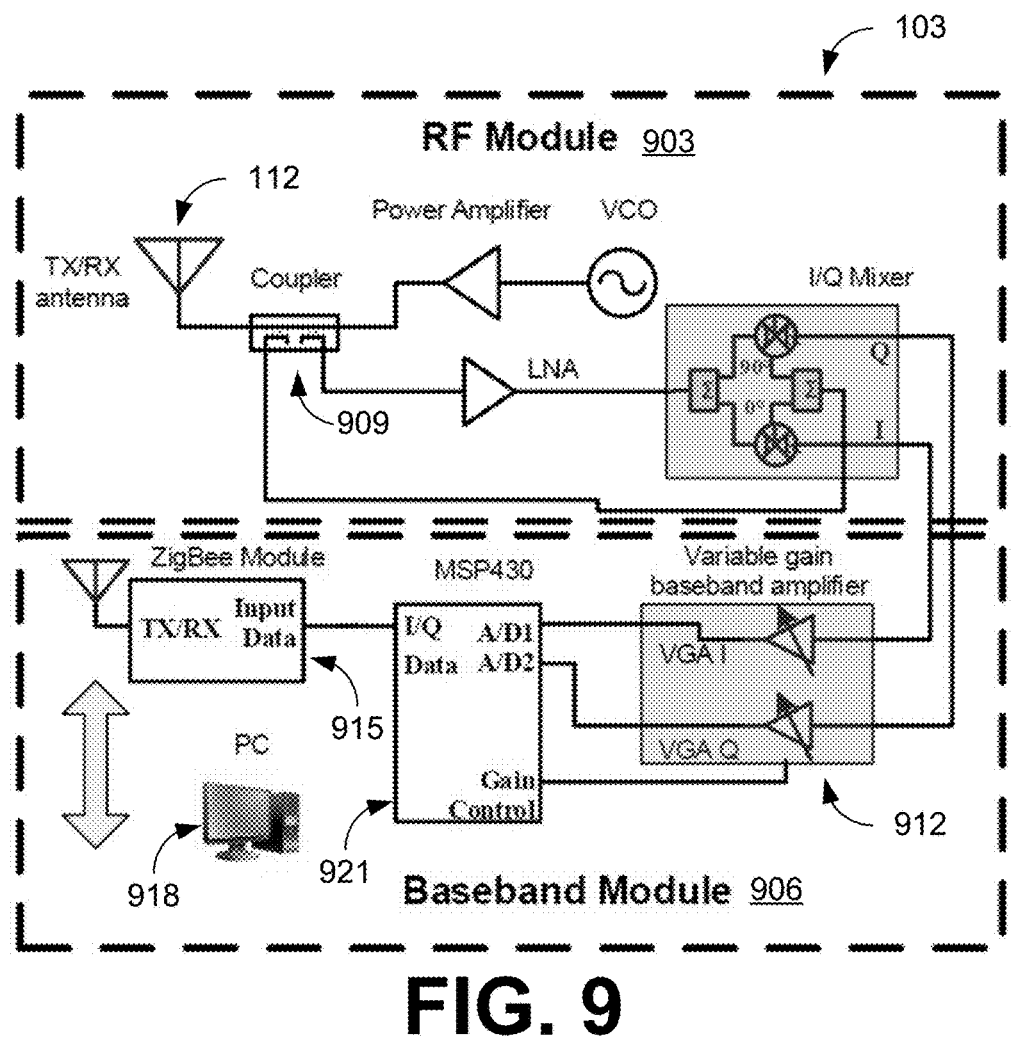
FIG. 9 is a block diagram illustrating an example of a portable radar system for vital sign detection, in accordance with various embodiments of the present disclosure.

The hardware platform of the vital sign radar system 103 can be designed for portable applications. Referring to FIG. 9, shown is a block diagram of an example of the portable radar system 103 for vital sign detection, which is implemented by two modules: a radio frequency (RF) module 903 and a baseband module 906.

Figure 10:
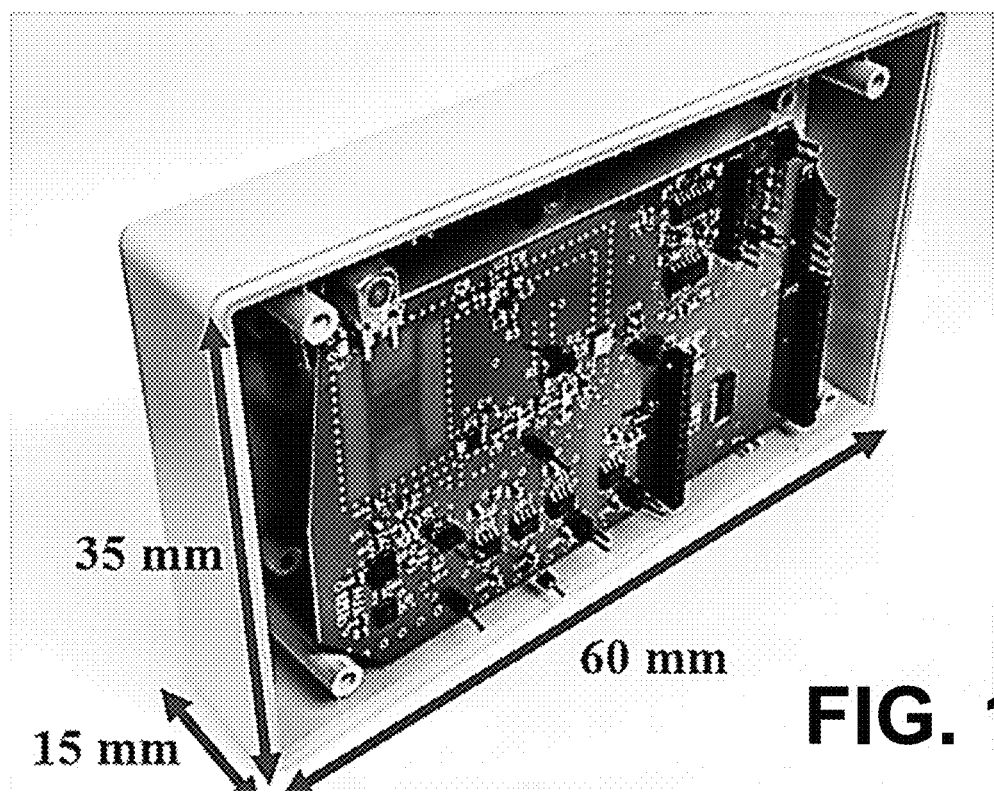
FIG. 10 is an image of the portable radar system of FIG. 9, in accordance with various embodiments of the present disclosure.

For the RF module 903, a T-model branch-line coupler 909 can be implemented on a printed circuit board (PCB) so that the sensor can use the same antenna 112 for transmitting and receiving the RF signals (e.g., at 5.8 GHz). This can help reduce the size of the detection system. For the baseband module 906, a variable gain amplifier (VGA) 912 can be implemented to amplify in-phase and quadrature (I/Q) signals with the proper gain. The VGA 912 can allow the system adapt to different acquisition distances. Besides, a ZigBee wireless module 915 can be integrated on board to transmit the I/Q data to a PC 918 for signal processing. FIG. 10 is an image of an implemented radar sensor in a 60 mm×35 mm×15 mm plastic box. The hardware platform can be sealed in the plastic box and powered by a battery. The detection system offers a compact size and good mobility, which makes it suitable as a portable device for non-contact vital sign detection.

Figure 11:
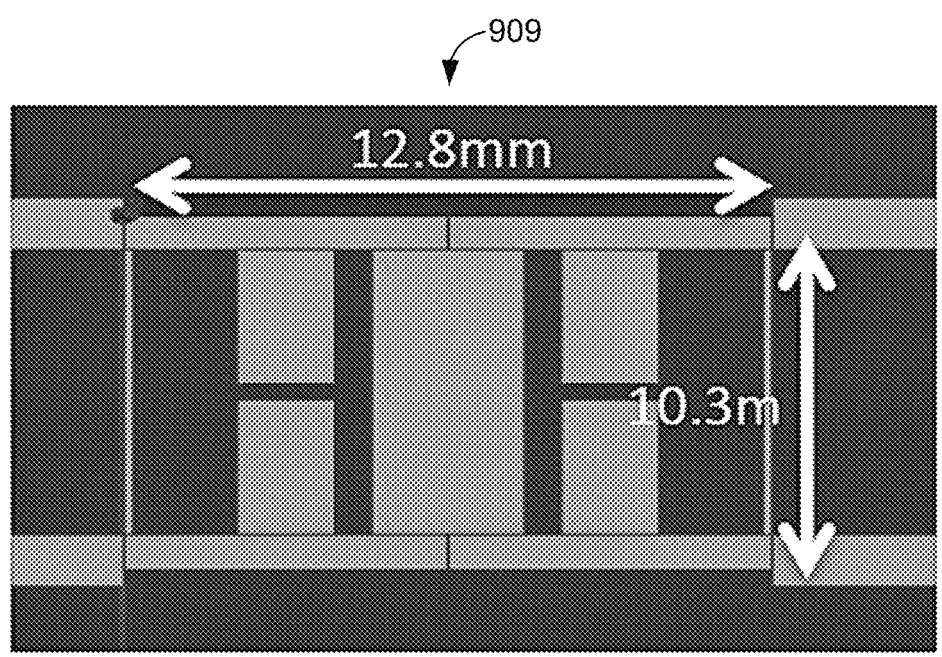
FIG. 11 is an image of a T-model branch-line coupler of the portable radar system of FIG. 9, in accordance with various embodiments of the present disclosure.
Figure 12A:
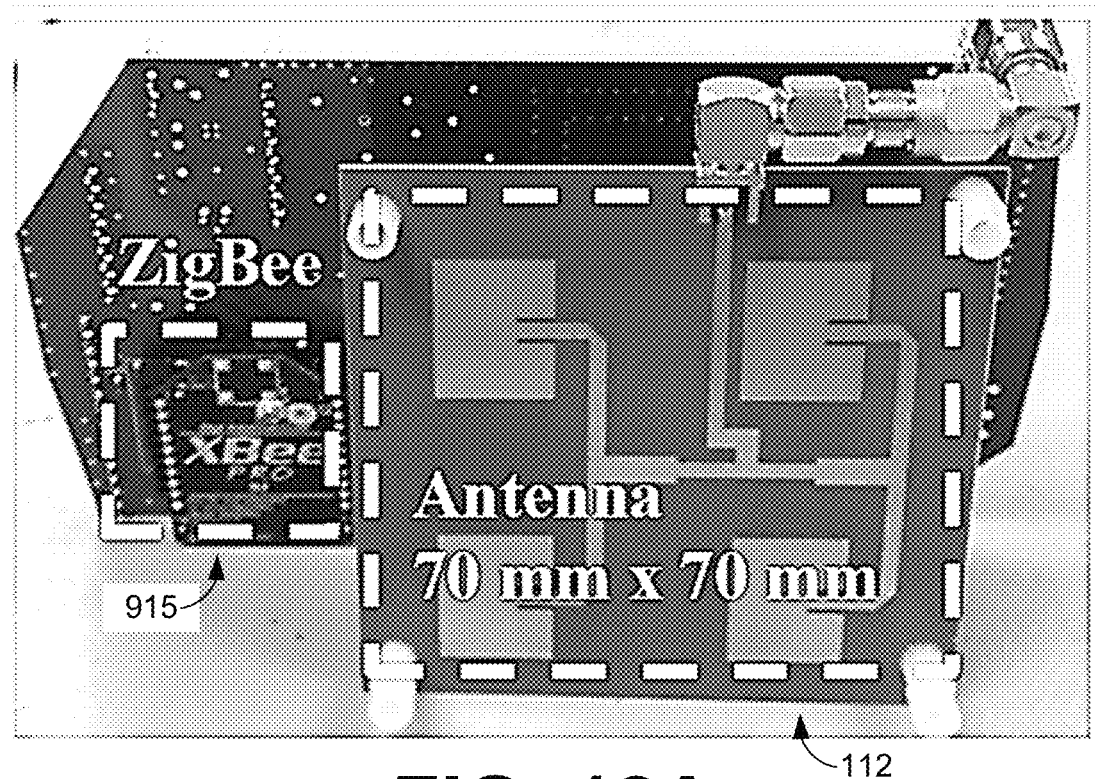
FIGS. 12A and 12B are images of the portable radar system of FIG. 9, in accordance with various embodiments of the present disclosure.

T-model branch-line coupler. The T-model branch-line coupler 909 can be implemented on the PCB to separate the transmitting and receiving RF signals 106 and 115. FIG. 11 is an image of an example of a T-model branch-line coupler 909. With the coupler 909, the radar system 103 can use one antenna 112 for TX/RX instead of using two separated antennas in its RF front end. At 5.8 GHz, the typical size of a 2×2 patch array antenna is 70 mm×70 mm as shown in FIG. 12A, which is much bigger than the size of the coupler (12.8 mm×10.3 mm). The coupler 909 can reduce the size of the hardware platform by using the same antenna 112 for both RF signal transmission and reception.

Figure 12B:
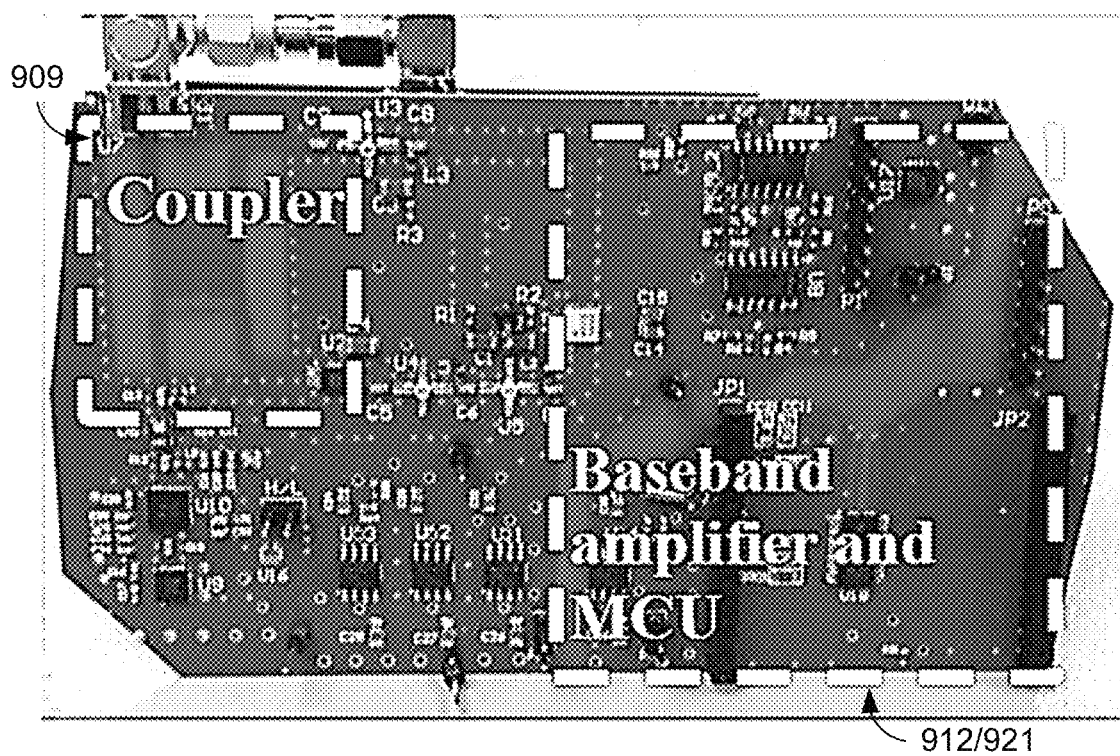

Automatic gain controlled baseband amplifier. The distance between the subject 109 (FIG. 8) and the radar sensor 112 can vary across the measurements. Different measurement distances can cause different strengths of the backscattered signal 115 (different $A_r$ in equation (8)). This will lead to different amplitudes of the demodulated I/Q signal ($A_I$ in equation (10) and $A_Q$ in equation (11)). A fixed gain baseband amplifier cannot adjust its gain according to the variation of signal strength, since it would either cause signal saturation or insufficient amplification of the I/Q signals. So the sensor can provide an adjustable amplifying gain to avoid signal saturation while fully utilizing the dynamical range of the A/D converter. In the example of FIG. 9, a variable gain baseband amplifier 912 is implemented. A microcontroller unit (MCU) 921 (e.g., Texas Instruments MSP430) can be used to monitor the dynamic range of the I/Q signals and adjust the gain of the baseband amplifier 912 to provide sufficient gain for amplification. FIG. 12A shows the front side view of the radar sensor hardware including circuitry for the ZigBee module 915 and the antenna 112, and FIG. 12B shows the back side view of the radar sensor hardware including circuitry for the coupler 909, the baseband amplifier 912 and MCU 921.

Figure 13:
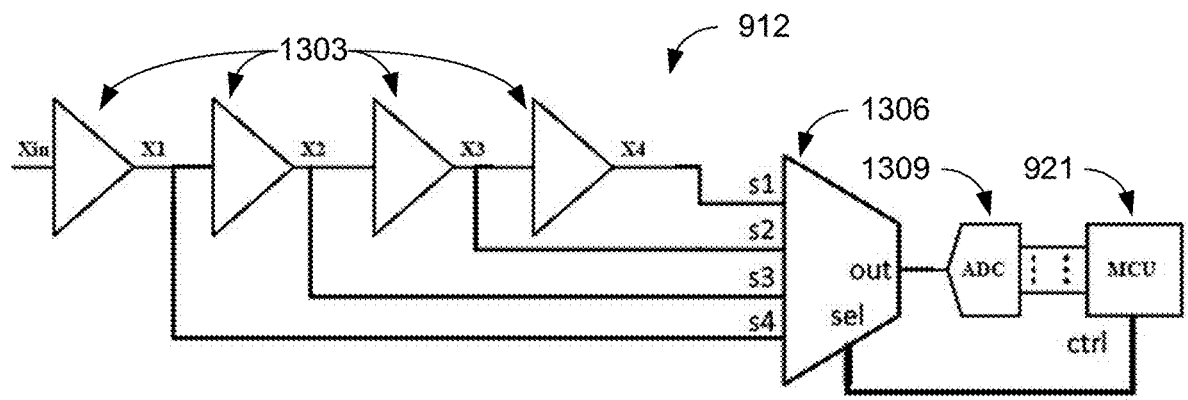
FIG. 13 is a schematic diagram illustrating an example of a variable gain amplifier (VGA) of the portable radar system of FIG. 9, in accordance with various embodiments of the present disclosure.

Referring next to FIG. 13, shown is a block diagram illustrating an example of the automatic gain controlled baseband amplifier 912 controlled by the MCU 921. The baseband amplifier 912 can be implemented by cascading four operational amplifier stages 1303. Each stage 1303 provides a fixed gain for amplifying I/Q signals. The four outputs (X1 to X4 in FIG. 13) of the baseband amplifier can provide separate gains of 5×, 10×, 20×, and 100×. A multiplexer 1306 controlled by MCU 921 (MSP430) is used to select the signal from the four outputs (X1 to X4 in FIG. 13) for analog-to-digital (A/D) sampling 1309.

Figure 14:
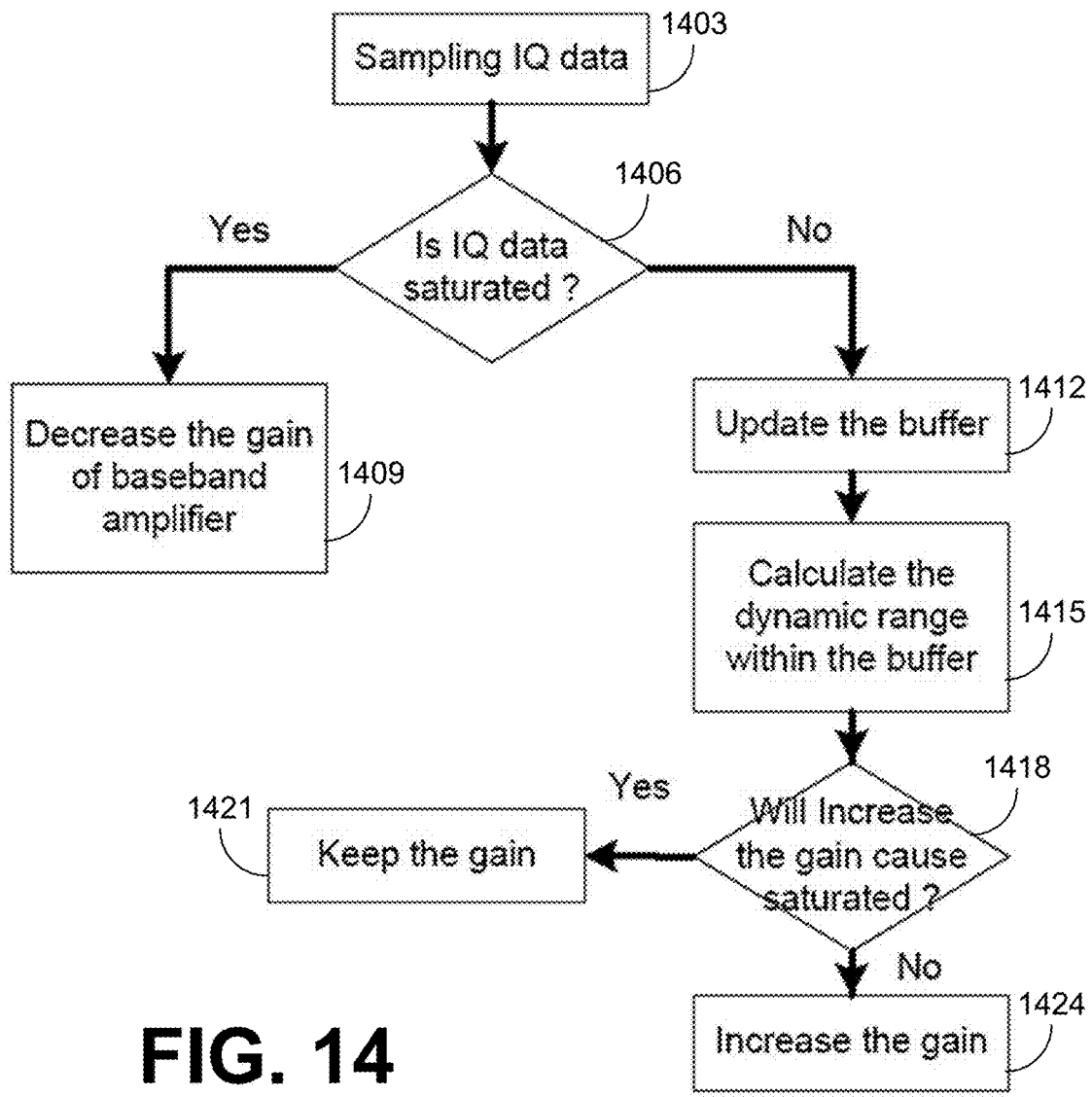
FIG. 14 is a flow chart illustrating an example of the adjustment of the VGA of FIG. 13, in accordance with various embodiments of the present disclosure.

The MCU 921 can be programmed to monitor the dynamic range of the output of the amplifier 912 and adjust its gain to avoid baseband signal saturation. FIG. 14 shows a flow chart illustrating an example of the automatic gain control. Beginning with 1403, the MCU 921 buffers an 8-second I/Q data sample from the output of the amplifier 912 and tracks the dynamical range of the signals within the buffered window. At 1406, the MCU 921 determines if the I/Q data is saturated or not. If the MCU 921 detects that the I/Q signals are getting saturated after the amplification, the MCU 921 can decrease the gain to a lower level at 1409. If the dynamic range of the signal is too small, the MCU 921 can provide a control signal that will boost the gain of the amplifier 912 by switching to an amplifier stage with larger gain. This can be accomplished by updating the buffer at 1412 and calculating the dynamic range within the buffer at 1415. If an increase in the gain would cause saturation at 1418, then the gain is kept the same at 1421. If the increase would not result in saturation at 1418, then the gain is increased at 1424. The flow can return to 1403 to continue monitoring the output of the amplifier 912. Using this automatic gain control mechanism, the baseband module 906 can adapt itself to different measurement distances and/or different signal strengths.

An algorithm can be implemented for fast vital sign acquisition which can be executed on a computing device such as the PC 918 of FIG. 9 to process the I/Q data sent from the portable radar sensor. The vital sign acquisition can effectively separate the heartbeat signal from the respiration signal. It can estimate one or more vital signs of the subject 109 by calculating the peak-to-peak intervals from the processed heartbeat and respiration waveforms.

Figure 15:
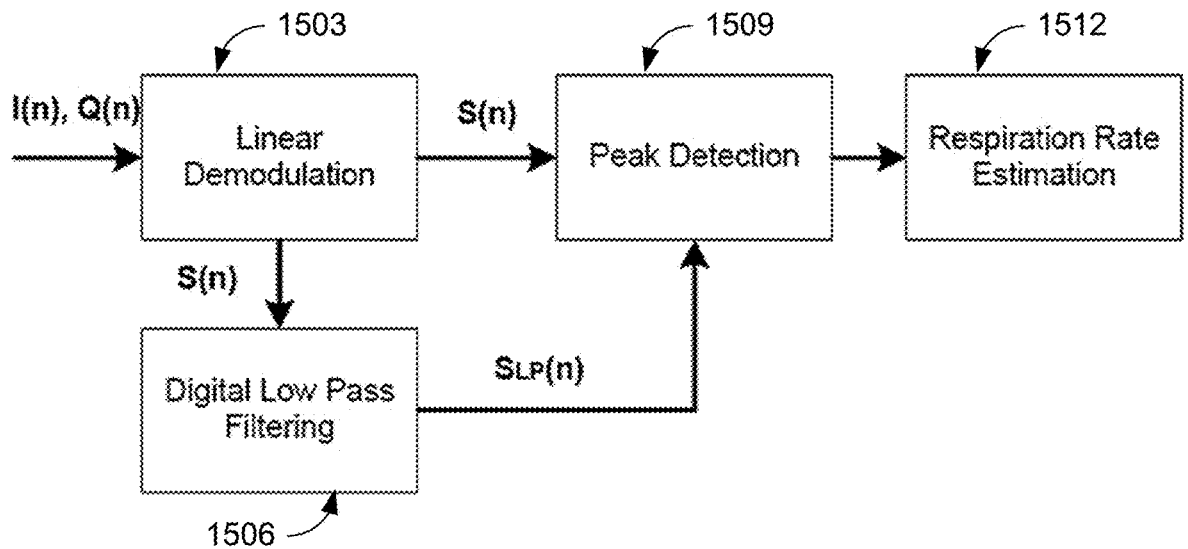
FIG. 15 is a flow chart illustrating an example of estimating the respiration rate of a subject, in accordance with various embodiments of the present disclosure.

Respiration rate estimation. Referring to FIG. 15, shown is a flow chart illustrating an example of estimating the respiration rate of a subject 109 (FIG. 9). The digitalized baseband signals I(n) and Q(n) can be demodulated into a phase signal S(n) using linear demodulation 1503. The signal S(n) can first go through a digital low pass filter 1506 to get $S_{LP}$ (n). A 3rd order Butterworth low pass filter with 1 Hz cutoff frequency can be used to depress high frequency noise and the heartbeat signal. The cutoff frequency is set to 1 Hz so that the typical respiration signal (e.g., a typical respiration rate of less than 60 bpm) can pass through. The filtered signal $S_{LP}$(n) is dominated by the fundamental harmonic of the respiration signal.

Figure 16A:
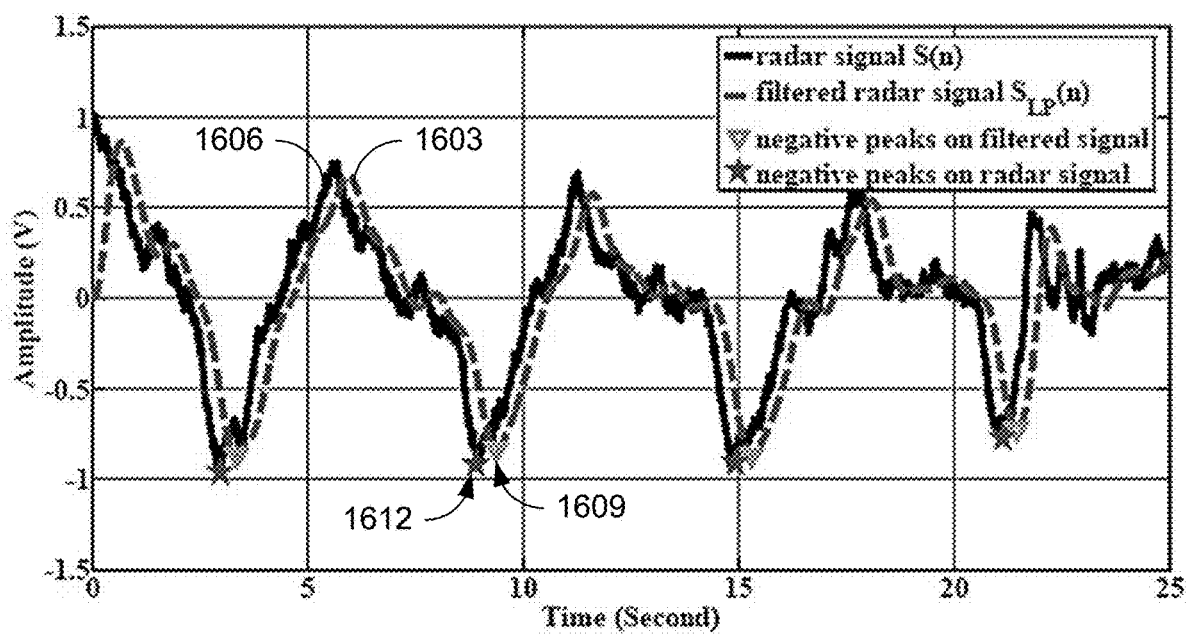
FIGS. 16A and 16B illustrate the respiration rate estimation, in accordance with various embodiments of the present disclosure.
Figure 16B:
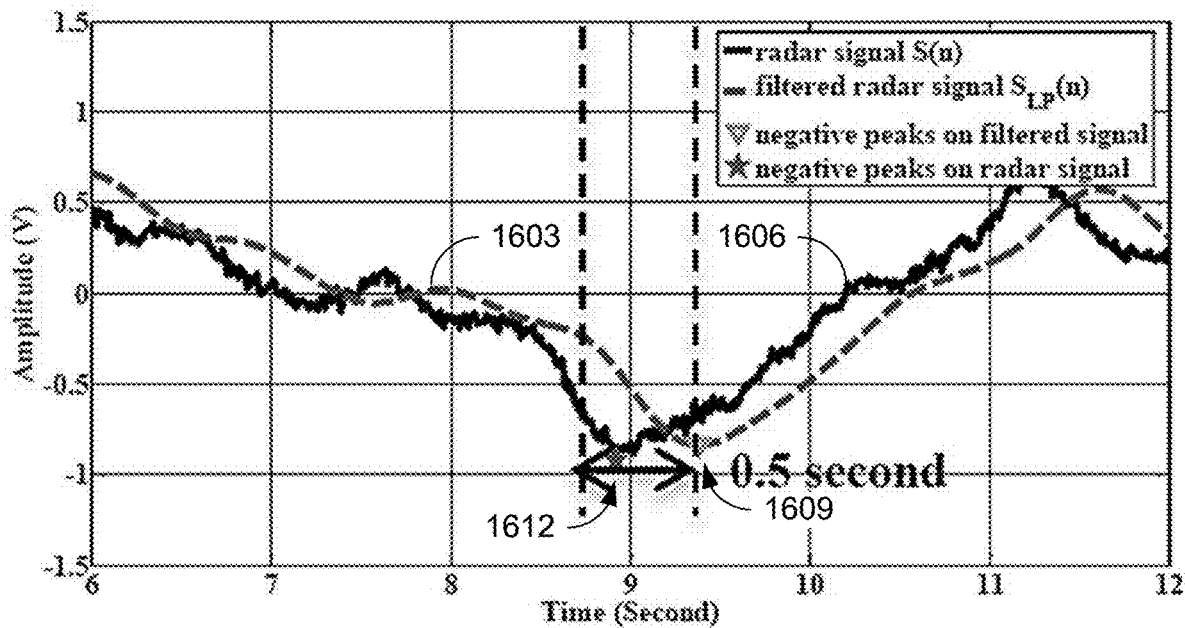

The S(n) and/or the $S_{LP}$ (n) can be used by the peak detection 1509 to detect respiration peaks. The respiration rate is estimated 1512 with the peak-to-peak intervals of the respiration waveform. As shown in FIGS. 16A and 16B, the peak detection 1509 for the respiration signal can be based on the filtered waveform $S_{LP}$(n) 1603 and the radar waveform S(n) 1606. The peak detection 1509 first detects the negative peaks 1609 on the filtered signal $S_{LP}$(n) with a three-point peak detection method. Since high frequency noise and heartbeat signals have been filtered out from $S_{LP}$(n), the peak detection 1509 on $S_{LP}$(n) is more reliable.

Thresholding can be used to remove the detected low amplitude peaks caused by noise. The peaks 1609 detected in $S_{LP}$(n) are then used to locate the respiration peak locations 1612 in S(n). The negative respiration peaks 1612 are regarded as the local minima points of S(n) within the 0.5-second detection window. The detection window is right in front of the peaks 1609 from $S_{LP}$(n) as illustrated in FIG. 16B. By using both the filtered signal $S_{LP}$(n) 1603 and the radar signal S(n) 1606 for peak detection, the peak detection is able to avoid high frequency noise peaks and accurately locate the respiration peaks 1612. The detected negative peaks 1612 can used to estimate the respiration rate of the subject.

Figure 17:
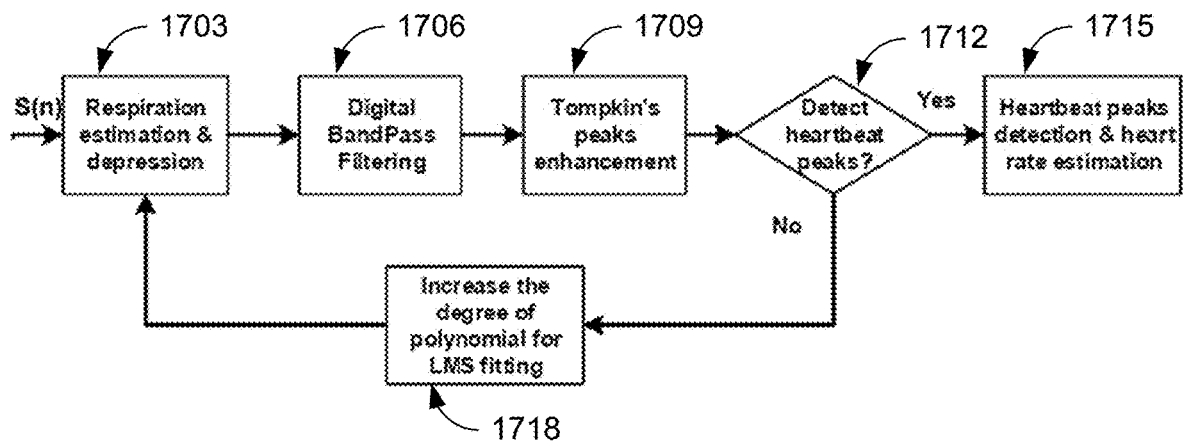
FIG. 17 is a flow chart illustrating flow chart illustrating an example of estimating the heart rate of the subject, in accordance with various embodiments of the present disclosure.

Heart rate estimation. FIG. 17 shows a flow chart illustrating an example of estimating the heart rate of the subject. First, the respiration signal in S(n) 1606 is fit and subtracted away at 1703. The remaining signal is then passed through digital bandpass filtering 1706 and Tompkins peak enhancement 1709 to extract and enhance the heartbeat pulses. After heartbeat pulses are extracted, peak detection 1712 is used to detect the locations of heartbeat peaks for heart rate estimation 1715. The fitting degree can also be adaptively changed 1718 to improve the quality of extracted heartbeat pulses.

Depression of respiration signal. The baseband radar waveform S(n) 1606 can be presented as:

$$S(n)=X_r(n)+X_h(n)+N(n). \tag{13}$$

where $X_r(n)$ is the respiration signal, $X_h(n)$ is the heart rate signal and $N(n)$ is the noise. For subjects 109 (FIG. 1) that are sitting still, the amplitude of the heartbeat vibration on front chest is on the order of 0.1 mm while the amplitude of respiration varies from about 4 mm to about 12 mm. Generally, the respiration signal $X_r(n)$ is not a single tone signal but a signal with strong higher order harmonics. The higher order harmonics of $X_r(n)$ can be stronger than the fundamental tone of heartbeat. In spectrum analysis, the higher order components of the respiration can smear or even overwhelm the heartbeat signal, causing error for heart rate estimation. Besides, the respiration movement of a subject 109 may not be strictly periodic. These can cause estimation errors for methods based on FFT spectrum analysis.

A Least Mean Square (LMS) method can be used to estimate the respiration signal. Since the respiration component is much stronger than the heartbeat component ($X_r(n) \gg X_h(n)$), the fitted result $\overline{X_r(n)}$ 1803 will be dominated by $X_r(n)$. Thus, by subtracting the fitted waveform $\overline{X_r(n)}$ from S(n) 1606, a large fraction of respiration waveform $X_r(n)$ (e.g., its fundamental and higher order harmonics) can be depressed.

Figure 18A:
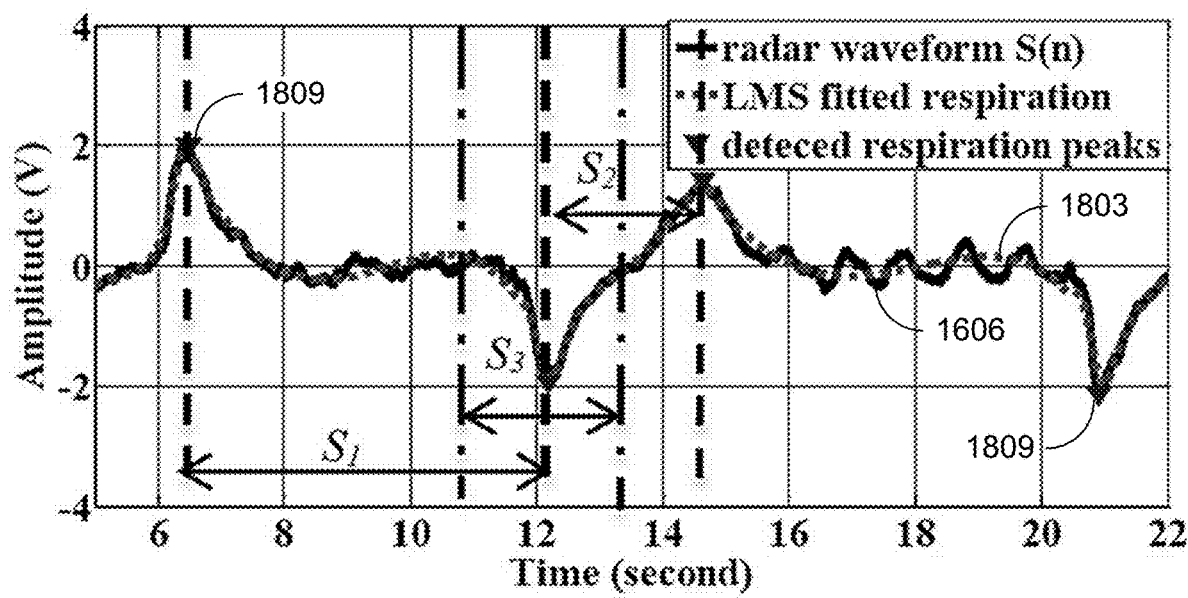
FIGS. 18A and 18B illustrate the heart rate estimation, in accordance with various embodiments of the present disclosure.

The procedure for LMS fitting on the signal S(n).1606 can be illustrated using FIG. 18A. Each respiration period can separated into three segments ($S_1$, $S_2$, and $S_3$ in FIG. 18A) using the detected respiration peaks 1809. The segments $S_1$, $S_2$, and $S_3$ shown in FIG. 18A can then be fit separately with polynomial curves. The segmentation on the signal is to make the fitting more robust against the non-periodical respiration movements.

Let $S_i(n)$ i=1, 2, 3 represent the data of the three segments in FIG. 18A, and let:

$$S_1 = [S(n_1) \; S(n_1+1) \; \ldots \; S(n_3)]^T, \tag{14}$$
$$S_2 = [S(n_3) \; S(n_3+1) \; \ldots \; S(n_5)]^T,$$
$$S_3 = [S(n_2) \; S(n_2+1) \; \ldots \; S(n_4)]^T,$$

where $n_1 < n_2 < n_3 < n_4 < n_5$. Let:

$$A_1 = \begin{bmatrix} 1 & n_1 & n_1^2 & \ldots & n_1^K \\ 1 & n_1+1 & (n_1+1)^2 & \ldots & (n_1+1)^K \\ \vdots & \vdots & \vdots & \ddots & \vdots \\ 1 & n_3 & n_3^2 & \ldots & n_3^K \end{bmatrix}^T, \text{ and} \tag{15}$$

$$\vec{a} = [a_0 \; a_1 \; \ldots \; a_K]^T \tag{16}$$

where K is the order of the polynomial curve for fitting. With the LMS method, the coefficients of the fitted curve for $S_1$ can be determined as:

$$\vec{a} = (A_1^T A_1)^{-1} A_1^T * S_1, \tag{17}$$

and the fitted data is given by:

$$\overline{S_1} = A_1 * \vec{a}. \tag{18}$$

Similarly, we can get $\overline{S_2}$ and $\overline{S_3}$ from $S_2$ and $S_3$. $\overline{S_1}$, $\overline{S_2}$ and $\overline{S_3}$ can then be merged together to get the fitted result $\overline{S_{seg}}$ of the respiration period:

$$\overline{S_{seg}(n)} = (1-w_1)*[\overline{S_1}, \overline{S_2}] + w_1 * \overline{S_3'}, \tag{19}$$

where $$\overline{S_3'}(n) = \begin{cases} \overline{S_3}(n) & \text{for } n = n_2 \ldots n_3 \\ 0 & \text{otherwise} \end{cases}, \tag{20}$$

$$w_1(n) = \begin{cases} \dfrac{n-n_2}{n_3-n_2} & \text{for } n = n_2 \ldots n_3 \\ \dfrac{n_4-n}{n_4-n_3} & \text{for } n = n_3+1 \ldots n_4 \\ 0 & \text{otherwise} \end{cases}, \tag{21}$$

$\overline{S_{seg}(n)}$ for different respiration periods are then conjunct together to get the estimated respiration waveform $\overline{X_r(n)}$.

Figure 18B:
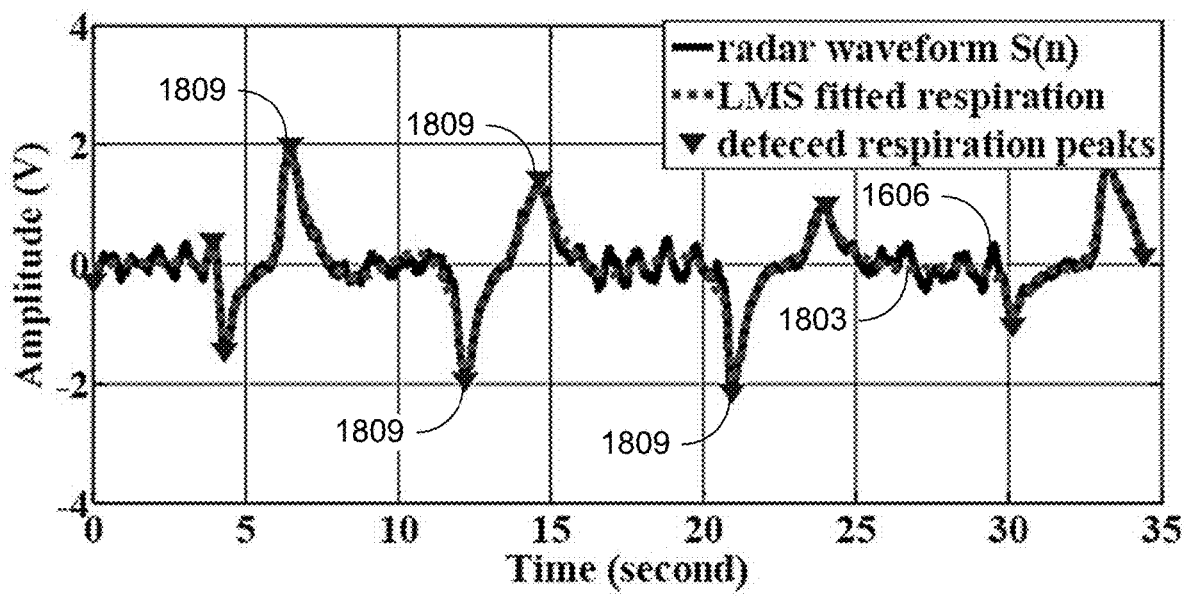

It can be seen from FIG. 18B that the fitted signal $\overline{X_r(n)}$ 1803 follows the trend of respiration in S(n) 1606 while ignores the small ripples due to heartbeats. The estimated respiration component $\overline{X_r(n)}$ 1803 can then be subtracted from S(n) to depress the respiration signal. The remaining signal of:

$$R(n)=S(n)-\overline{X_r(n)} \tag{22}$$

represents the heartbeat pulses, the fitting error, and high frequency noise.

Band pass filtering. After the cancellation of the respiration signal, the remaining signal R(n) is filtered via a band pass filter 1706 (FIG. 17) such as, e.g., a 3.5 Hz to 12 Hz passband. The band pass filtering 1706 can depress high frequency noise and the fundamental harmonic of the heartbeat signal $X_h(n)$. Higher order harmonics of $X_h(n)$ can be used for fast heart rate estimation. The reason of using higher order harmonics instead of the fundamental harmonic for heart rate estimation can be understood by analyzing the uncertainty principle. For a heartbeat signal $X_h(n)$ with a fundamental frequency $f_{heart}$, if it is estimated with a T-second measurement window, the FFT spectrum resolution will be:

$$\Delta f = 1/T. \tag{23}$$

So if the estimation of the heart rate is based on its fundamental harmonic, a short measurement time T will lead to worse accuracy (or a bigger $\Delta f$ in equation (23)). In this case, accurate heart rate estimation within a short time is not possible. However, if the algorithm is based on the Nth order harmonic of the heartbeat signal with frequency $f_{Nheart}=N*f_{heart}$. For a T-second measurement, the uncertainty for $f_{Nheart}$ in the spectrum will be:

$$\Delta f_{Nheart}=1/T, \tag{24}$$

and since:

$$f_{heart}=f_{Nheart}/N, \tag{25}$$

the uncertainty of $f_{heart}$ becomes:

$$\Delta f_{heart}=\Delta f_{Nheart}/N=1/NT. \tag{26}$$

Thus, methods based on higher order harmonics for heart rate estimation can get a better accuracy for a short time measurement.

Tompkins's method for heartbeat pulses extraction. After the bandpass filtering 706, the filtered signal y(n) can be enhanced via Tompkins's method 1709 (FIG. 17). The method 1709 enhances the heartbeat signal via steps including derivative, square, and averaging operations as illustrated in FIG. 2. Tompkins's method first calculates the derivative of signal y(n) at 203 by:

$$z[n] = \frac{f_s}{8} * \{-y[n-2] - 2y[n-1] + 2y[n+1] + y[n+2]\}, \quad (27)$$

where $f_s$ is the sample rate of the data. Then, z[n] can be used to calculate a squared waveform a[n] at 206 by:

$$a[n] = y[n]^2. \quad (28)$$

The averaged 209 waveform x[n] can be derived at 209 from a[n] by averaging a[n] with a 0.3 second window:

$$x[n] = \frac{1}{0.3 * f_s} \sum_{i=n+1}^{n+0.3*f_s} a[n]. \quad (28)$$

Figure 19A:
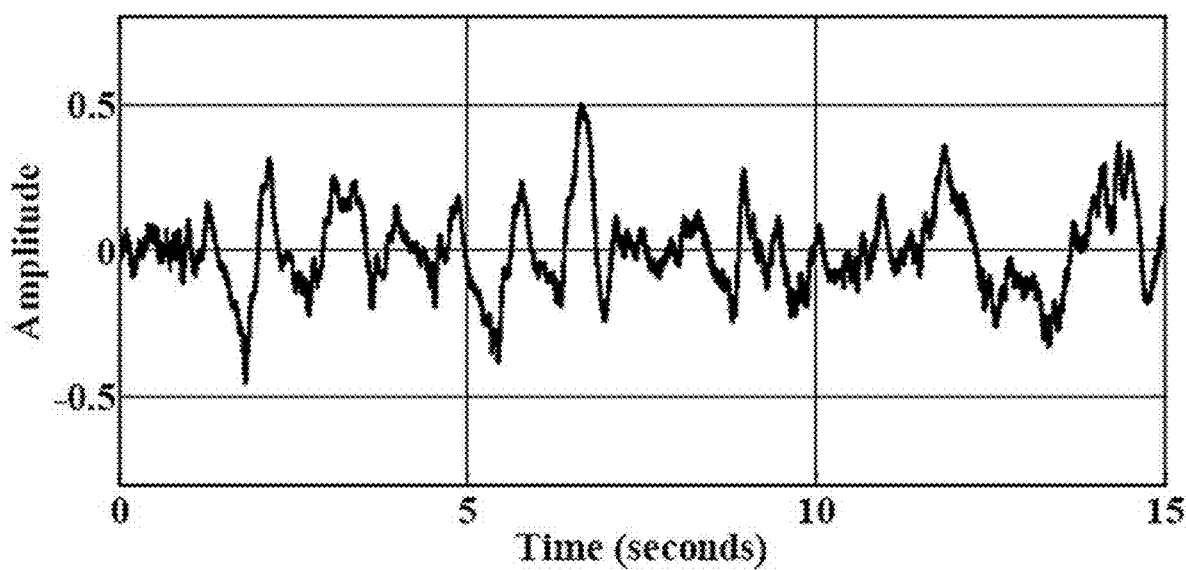
FIGS. 19A through 19D illustrate examples of waveforms of Tompkins peak detection and enhancement, in accordance with various embodiments of the present disclosure.
Figure 19B:
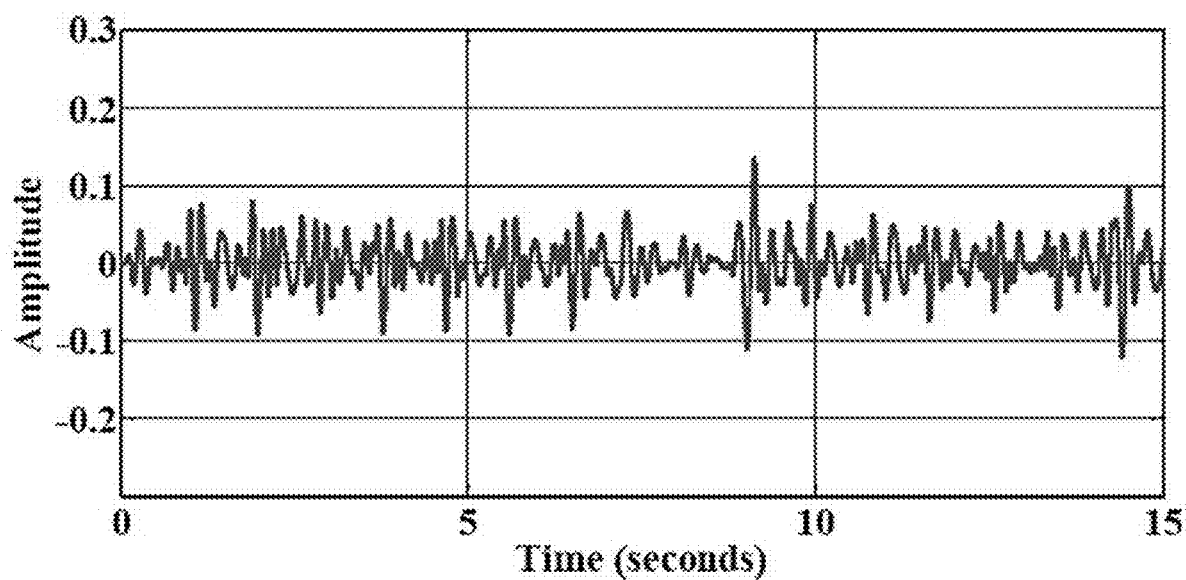
Figure 19C:
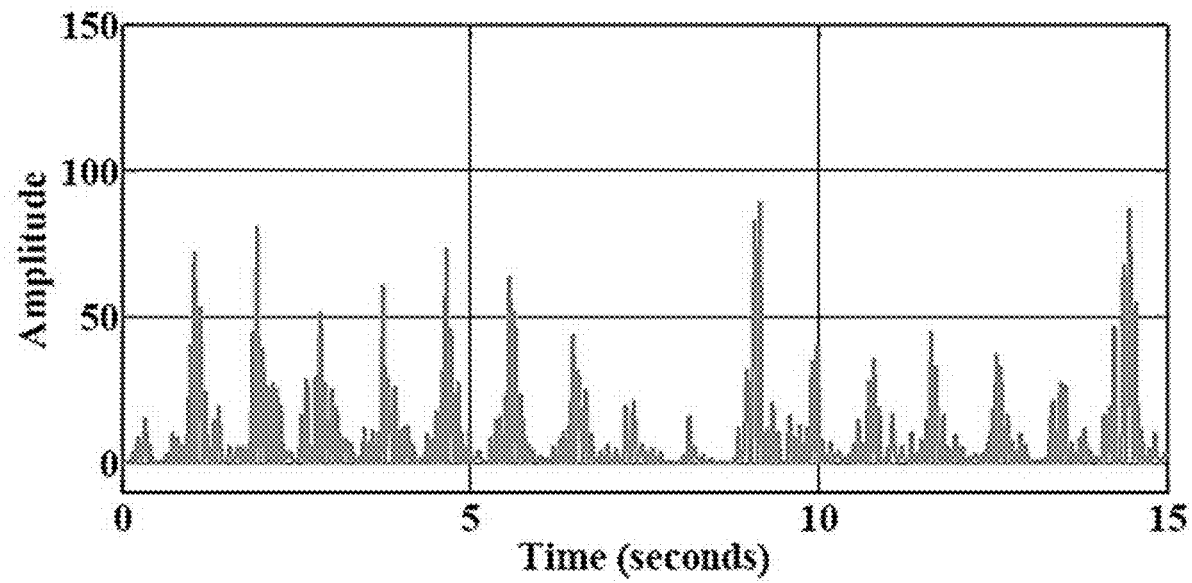
Figure 19D:
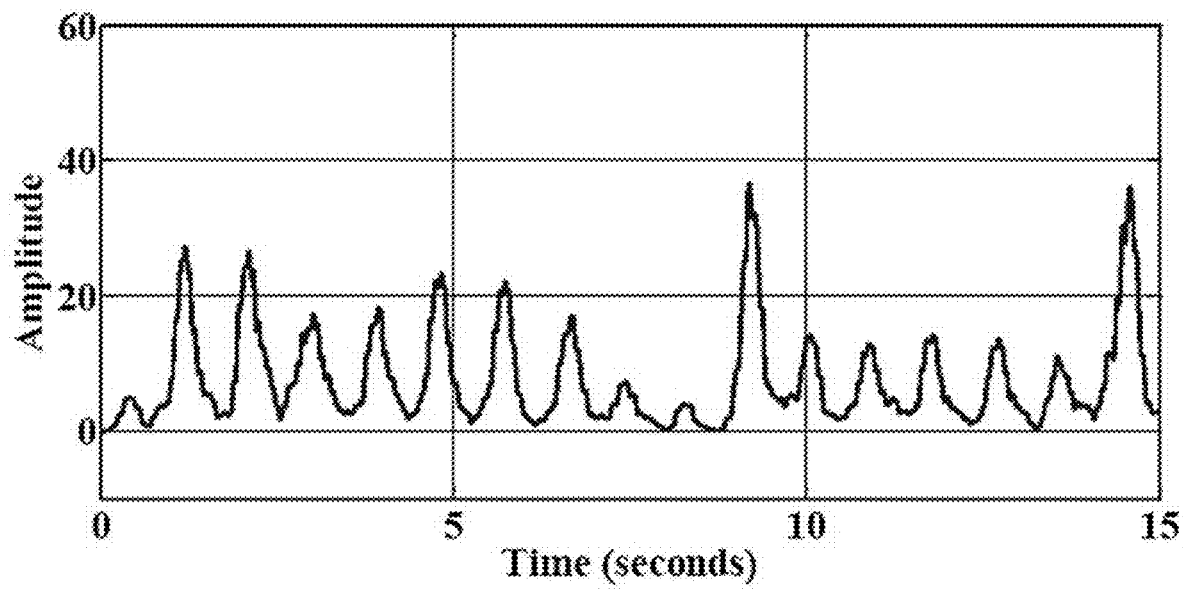

Waveforms in each step of Tompkins's method can be seen in FIGS. 19A-19D. FIG. 19A shows an example of the waveform R(n) after subtraction, FIG. 19B shows an example of the bandpass filtered waveform y(n), FIG. 19C shows an example of the squared waveform a(n), and FIG. 19D shows an example of the averaged waveform x(n). By using the Tompkins's method, the heartbeat pulses in y(n) can be enhanced for heartbeat peak detection.

If the quality of extracted heartbeat pulses is not good enough for accurate heart rate estimation (e.g., the variance of peak-to-peak intervals in the averaged waveform x[n] is above a preset threshold), the algorithm can redo the depression of respiration signal, band pass filtering, and Tompkins's method for heartbeat pulses extraction described above with higher order polynomial curves to improve the signal quality.

Figure 20:
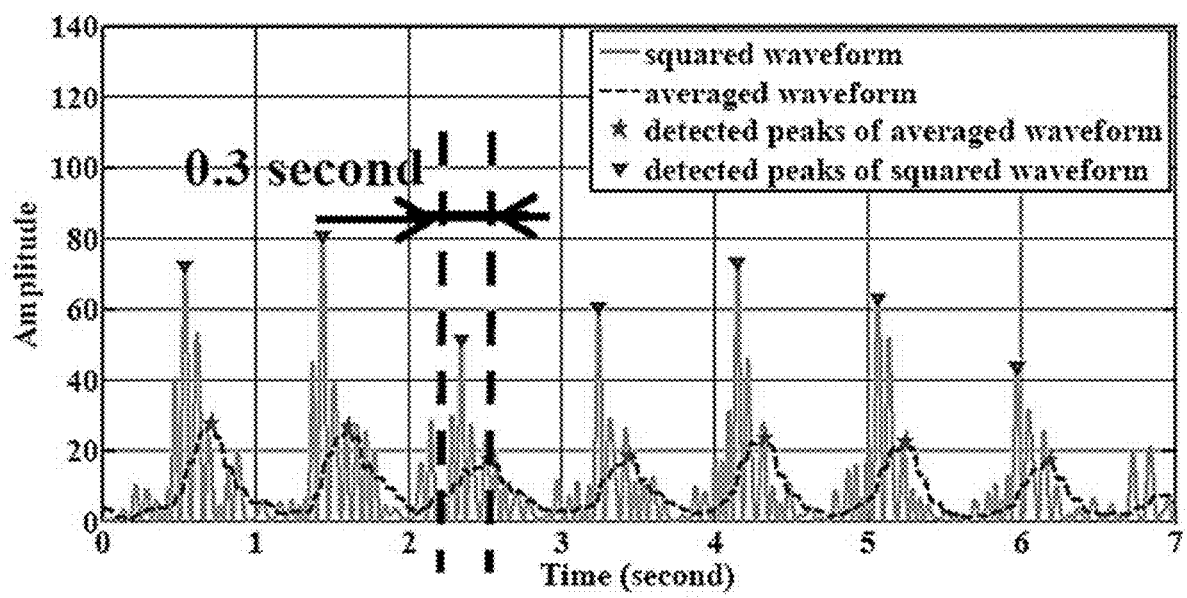
FIG. 20 illustrates an example of peaks detection using a squared waveform and averaged waveform, in accordance with various embodiments of the present disclosure.

Peak detection for heartbeat signal. The heartbeat peaks detection 1715 (FIG. 17) can be based on the squared waveform a[n] and the averaged waveform x[n]. FIG. 20 illustrates the peaks detection using squared waveform a[n] and averaged waveform x[n]. Since low energy noise spikes are depressed by averaging 209 (FIG. 2), the peak detection on x[n] is less sensitive for high frequency noise. But the heartbeat peaks in x[n] are smooth peaks with poor time resolution. The squared waveform a[n] in FIG. 19C in contrast has many noise peaks, even though it has a good time solution. So both a[n] and x[n] can be used to reliably detect the accurate locations of heartbeat peaks. Once the peaks are located in averaged waveform x[n], the heartbeat peaks in a[n] can be detected as the local maximal point within a detection window. The detection window can be a 0.3-second time slot right before the detected peaks in averaged waveform x[n] as shown in FIG. 20. The heart rate can then be estimated via the peak-to-peak intervals.

During the measurements, the subjects 109 sat 0.6 meter away from the vital sign radar 103 and were directed to keep their bodies still and breathe regularly. The sensor was adjusted to the height of the subjects' sternum for a better signal quality. A MEMS sensor (e.g., model sq-xld-3x) was affixed to the subjects' front chest for reference respiration measurements. A contact sensor (e.g., a model 1010 piezoelectric pulse transducer) was attached to the subjects' finger to provide the reference heart rate signal.

Both the respiration and heartbeat measurement results are presented. The time windows for estimating heart rate and respiration rate were different. For heart rate estimation, a 5 second window was used and for the respiration rate, the window length was extended to 10 seconds. The extension was due to the fact that the respiration is a low frequency signal (e.g., 0.15 to 0.4 Hz).

Figure 21A:
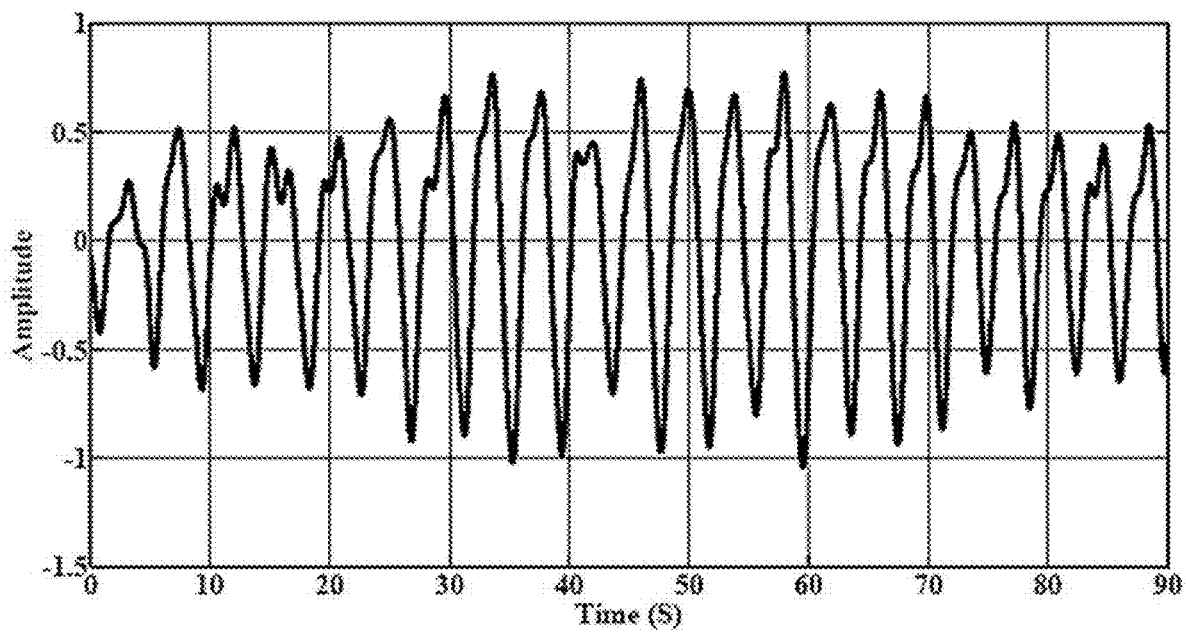
FIGS. 21A and 21B illustrate an example of respiration waveforms from the portable radar system of FIG. 9 and a MEMS sensor on the subject, in accordance with various embodiments of the present disclosure.
Figure 21B:
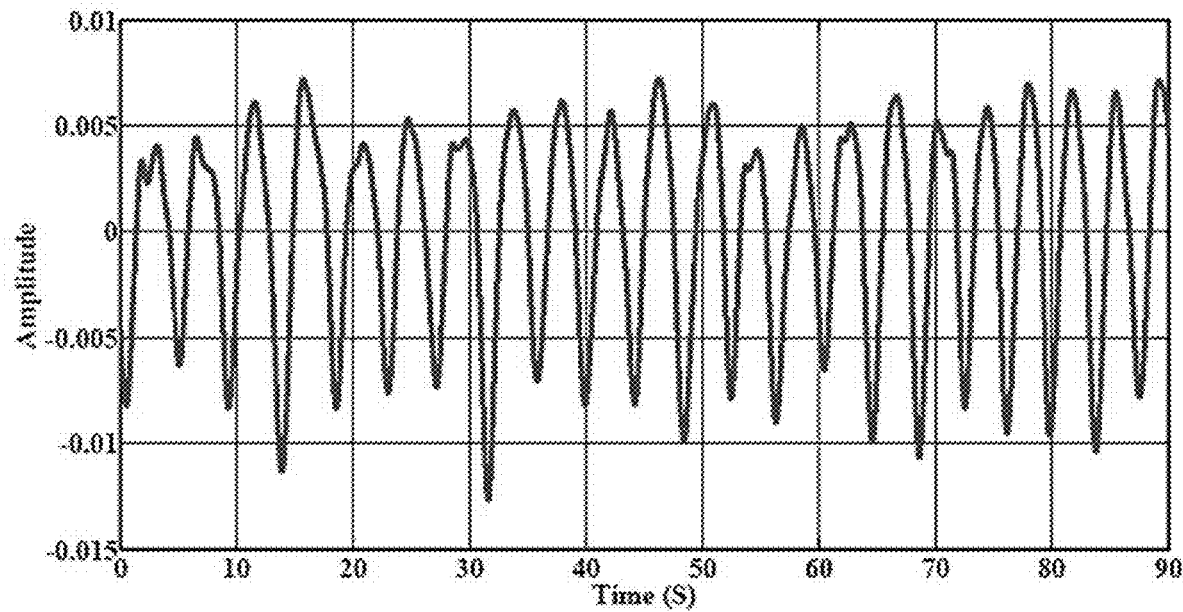
Figure 22:
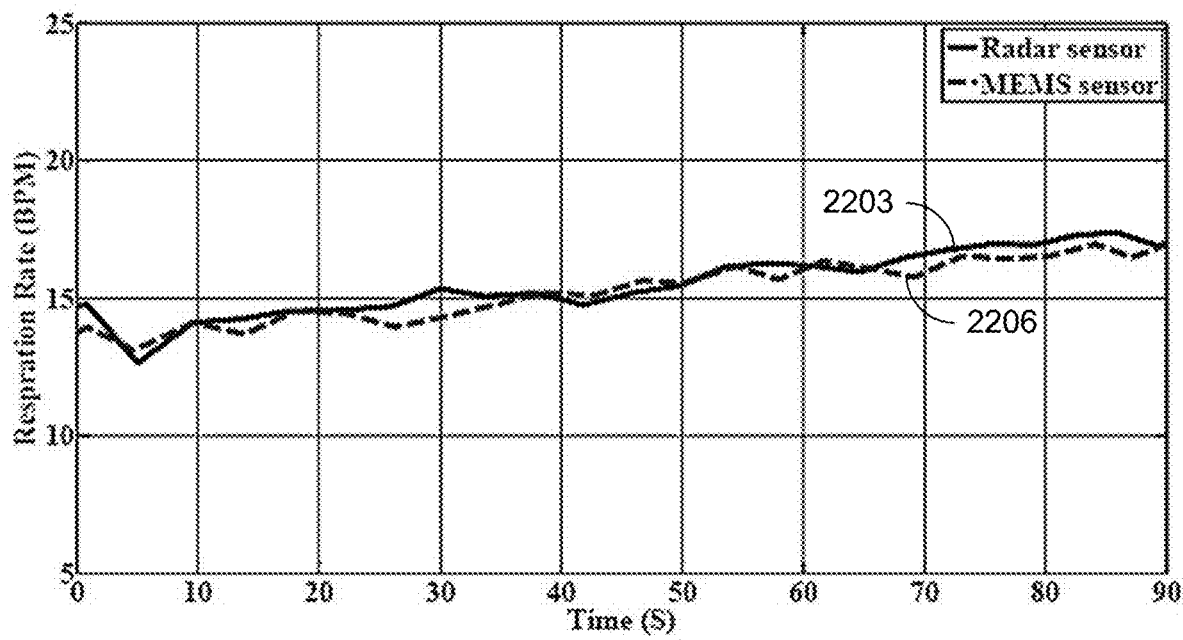
FIG. 22 illustrates an example of a comparison of estimated and measured respiration rates, in accordance with various embodiments of the present disclosure.

Respiration measurement. Referring to FIGS. 21A and 21B, shown are the respiration waveforms from the radar sensor and the MEMS sensor, respectively. The respiration rate can be estimated with the peak detection method discussed above. The algorithm can use a 10-second window to estimate respiration rate from both waveforms. The peak-to-peak intervals within the windows can be averaged for the respiration rate estimation. FIG. 22 shows the comparison of the respiration rates estimated by the radar sensor 2203 and the MEMS sensor 2206. The averaged difference of the measurements from the two sensors is 0.26 beat-per-minute (bpm) with a standard derivation of 0.543 bpm. The measurement shows that the radar sensor can provide an accurate measurement of the subject's respiration rate when compared to the reference MEMS sensor.

Figure 23:
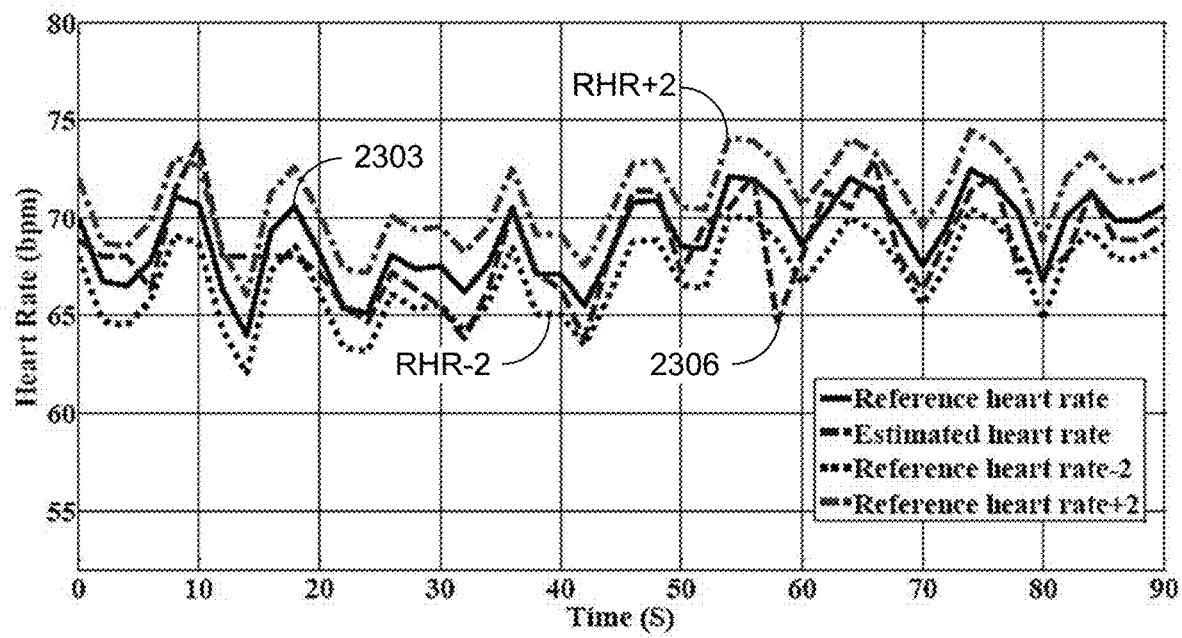
FIG. 23 illustrates an example of a comparison between reference and estimated heart rates, in accordance with various embodiments of the present disclosure.

Heart rate measurement. Referring to FIG. 23, shown is a comparison between the reference heart rate 2303 and the heart rate estimated via the radar sensor 2306. The sensor can use a 5-second measuring window for heart rate estimation. The short measurement window allows the sensor to have a quicker response for subjects' heart rate variation. The detected peak-to-peak heartbeat intervals within the window can be averaged for the heart rate estimation 2306. FIG. 23 shows traces corresponding to reference heart rate 2303 (estimated via the contact sensor) and reference heart rate±2 bpm (RHR+/−2) for comparison. Both the estimated heart rate 2306 and the reference heart rate 2303 were calculated with a 2-second incremental step size in the measurement. The averaged difference between the estimations from the two sensors is 0.52 bpm with a standard derivation of 1.84 bpm. It can be observed from FIG. 23 that the fast time domain algorithm can accurately estimate heart rate with a short measurement window. It can also reflect the short period heart rate variation like the contact sensor.

Figure 24:
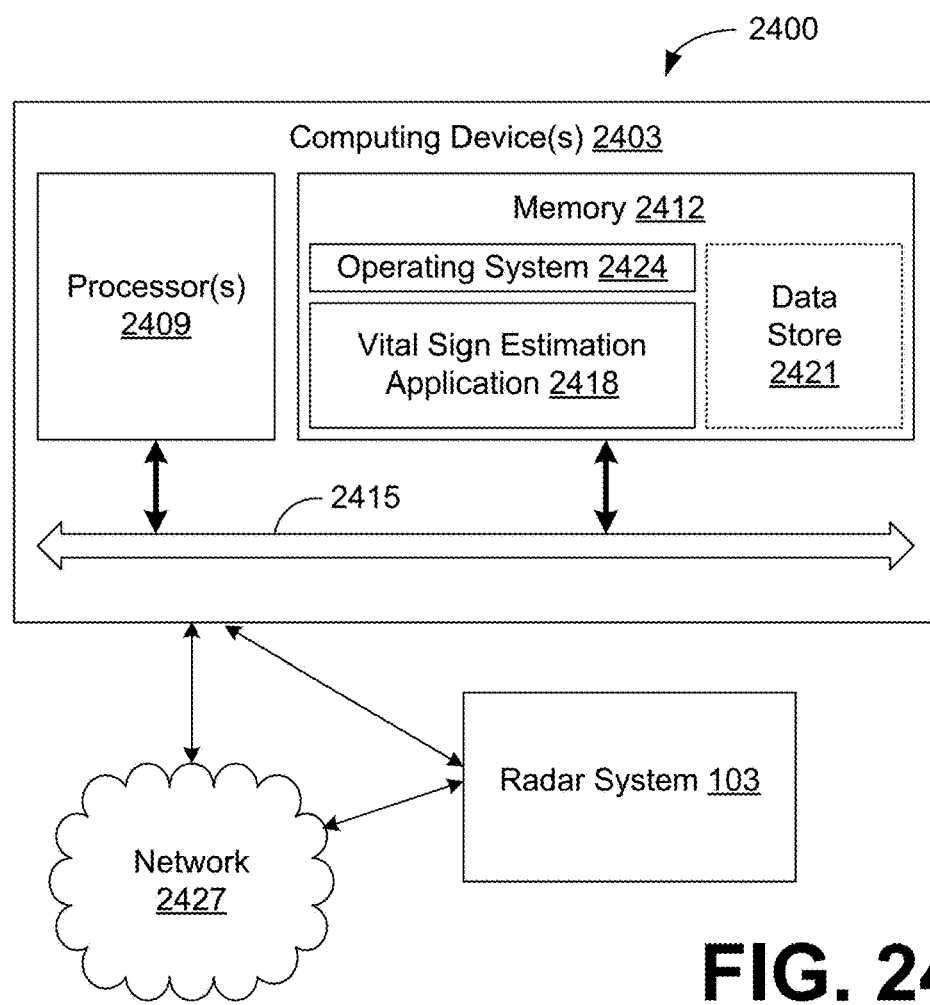
FIG. 24 is an example of a system that may be utilized in vital sign estimation, in accordance with various embodiments of the present disclosure.

Referring now to FIG. 24, shown is an example of a system 2400 that may be utilized in non-contact monitoring of vital signs. The system 2400 includes one or more computing device(s) 2403, one or more radar system(s) 103 that can provide non-contact measurement indications as previously discussed. For example, the radar system(s) 103 can monitor vibrations of a target subject such as a patient, or other individual or animal.

The computing device 2403 includes at least one processor circuit, for example, having a processor 2409 and a memory 2412, both of which are coupled to a local interface 2415. To this end, the computing device(s) 2403 may comprise, for example, a server computer or any other system providing computing capability. The computing device(s) 2403 may include, for example, one or more display devices such as cathode ray tubes (CRTs), liquid crystal display (LCD) screens, gas plasma-based flat panel displays, LCD projectors, or other types of display devices, etc. The computing device(s) 2403 may also include, for example various peripheral devices. In particular, the peripheral devices may include input devices such as, for example, a keyboard, keypad, touch pad, touch screen, microphone, scanner, mouse, joystick, or one or more push buttons, etc. Even though the computing device 2403 is referred to in the singular, it is understood that a plurality of computing devices 2403 may be employed in the various arrangements as described above. The local interface 2415 may comprise, for example, a data bus with an accompanying address/control bus or other bus structure as can be appreciated.

Stored in the memory 2412 are both data and several components that are executable by the processor 2409. In particular, stored in the memory 2412 and executable by the processor 2409 include a vital sign estimation application 2418 and potentially other applications. Also stored in the memory 2412 may be a data store 2421 and other data. The data stored in the data store 2421, for example, is associated with the operation of the various applications and/or functional entities described below. For example, the data store may include sample analysis results, corrective measures, and other data or information as can be understood. In addition, an operating system 2424 may be stored in the memory 2412 and executable by the processor 2409. The data store 2421 may be may be located in a single computing device or may be dispersed among many different devices.

The radar system 103 is representative of a plurality of devices that may be communicatively coupled to the computing device 2403 either directly through a wired or wireless connection such as, e.g., Zigbee® or Bluetooth®, or through a network 2427 such as, e.g., the Internet, intranets, extranets, wide area networks (WANs), local area networks (LANs), wired networks, wireless networks, or other suitable networks, etc., or any combination of two or more such networks. The radar system 103 may comprise, for example, a processor-based system such as a processing system or other application specific system with communication capabilities. In some embodiments, a radar system 103 may be directly connected to the computing device 2403.

The components executed on the computing device 2403 include, for example, the vital sign estimation application 2418 and other systems, applications, services, processes, engines, or functionality not discussed in detail herein. The computing device 2403 can receive information regarding the monitored subject from a radar system 103, which can then be evaluated by the vital sign estimation application 2418.

It is understood that there may be other applications that are stored in the memory 2412 and are executable by the processor 2409 as can be appreciated. Where any component discussed herein is implemented in the form of software, any one of a number of programming languages may be employed such as, for example, C, C++, C #, Objective C, Java, Java Script, Perl, PHP, Visual Basic, Python, Ruby, Delphi, Flash, or other programming languages.

A number of software components are stored in the memory 2412 and are executable by the processor 2409. In this respect, the term "executable" means a program file that is in a form that can ultimately be run by the processor 2409. Examples of executable programs may be, for example, a compiled program that can be translated into machine instructions in a format that can be loaded into a random access portion of the memory 2412 and run by the processor 2409, source code that may be expressed in proper format such as object code that is capable of being loaded into a random access portion of the memory 2412 and executed by the processor 2409, or source code that may be interpreted by another executable program to generate instructions in a random access portion of the memory 2412 to be executed by the processor 2409, etc. An executable program may be stored in any portion or component of the memory 2412 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The examples of FIGS. 2, 3, 15 and 17 show aspects of the architecture, functionality, and operation of a possible implementation of the vital sign estimation application. In this regard, each block can represent a module, segment, or portion of code, which comprises one or more executable instructions for implementing the specified logical function(s). It should also be noted that in some alternative implementations, the functions noted in the blocks may occur out of the order noted in FIGS. 2, 3, 15 and 17. For example, two blocks shown in succession in FIGS. 2, 3, 15 and 17 may in fact be executed substantially concurrently or the blocks may sometimes be executed in the reverse order, depending upon the functionality involved.

Also, the processor 2409 may represent multiple processors 2409 and the memory 2412 may represent multiple memories 2412 that operate in parallel processing circuits, respectively. In such a case, the local interface 2415 may be an appropriate network that facilitates communication between any two of the multiple processors 2409, between any processor 2409 and any of the memories 2412, or between any two of the memories 2412, etc. The local interface 2415 may comprise additional systems designed to coordinate this communication, including, for example, performing load balancing. The processor 2409 may be of electrical or of some other available construction.

Although the vital sign estimation application 2418, and other various systems described herein, may be embodied in software or instructions executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Any logic or application described herein, including the vital sign estimation application 2418, that comprises software or instructions can be embodied in any non-transitory computer-readable medium for use by or in connection with an instruction execution system such as, for example, a processor 2409 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

A portable radar system for fast vital sign acquisition has been presented. Both hardware and software of the system were designed to optimize the sensor's performance. The hardware platform of the system features a coupler 909 (FIG. 9) and an automatic gain controlled baseband amplifier 912 (FIG. 9). The hardware implementation makes the sensor compact and adapts to the variation of signal strength. A fast-acquisition algorithm was also designed for the system to shorten the system's response time. The algorithm was able to depress the respiration signal with polynomial fitting and extract the heartbeat pulses for peaks detection measurement. Experimental results show that the system can accurately estimate the subjects' physiology information within short measurement time windows, reflecting the short period heart rate variation as the contact sensor.

Embodiments of the vital sign extraction and estimation can be advantageous when a first vibration, such as respiration, has an amplitude that is greater than 5, greater than 10, greater than 15, and/or greater than 20 times an amplitude of a second vibration, such as heartbeat. In addition to these amplitude ratios, various embodiments can have a vibration rate of the first vibration that is smaller than the vibration rate of the second vibration (e.g., $\frac{1}{2}$, $\frac{1}{3}$, $\frac{1}{4}$, and/or $\frac{1}{5}$ of the second vibration rate). The transmit antenna and the receive antenna can be located several radar signal wavelengths away from the target. How far the transmit antenna and receive antenna are away from the target can depend on the transmitted power and the focused beam width of the antenna. In one embodiment, among others, the detection distance can be greater than 0.3, 0.5, 1.0, 1.5, 2.0, 2.5, and/or 3.0 m with a transmission frequency of 5.8 GHz and transmission power of 10 mW.

Embodiments can be applied to more than 2 vibrations when the amplitudes and vibration rates in the time domain are different enough to allow for identification of the individual vibration signals.

Embodiments can utilize quadrature detection, which can avoid null points in the measurements. Further embodiments can utilize non-quadrature detection. In some embodiments, the I-channel, Q-channel, the better signal of the I and Q-channels, or some combination of the I-channel and Q-channel, can be used as the signal representative of the receive signal, and the subject method of analyzing the chosen signal to identify at least two adjacent peaks of the first vibration, separating the chosen signal into segments between the adjacent peaks, fitting a curve fit to the first vibration, subtracting the curve fit from the chosen signal to produce a remaining signal, processing the remaining signal, processing the remaining signal to produce a processed remaining signal, wherein peaks of the second vibration are enhanced in the processed remaining signal, analyzing the processed remaining signal to identify at least two adjacent peaks of the second vibration, and determining the second vibration rate from the at least two adjacent peaks of the processed remaining signal, can be performed on such signal representative of the receive signal.

Embodiments can estimate the time interval between peaks of one of the vibrations, and convert this to a vibration rate, as taught. In further embodiments, the vibration rate can be estimated by estimating the time difference between two or more points in the vibration cycle, such as the time difference between two rising edges, the time difference between two falling edges, or the time difference between two other locations on the vibration signal, taking into account the portion of the period of the vibration represented. These peaks or other locations can be identified after differentiating the waveform.

Embodiments can be implemented via a variety of radar systems, including the radar systems shown in FIG. 1 from U.S. Pat. No. 7,848,896, FIG. 1 from U.S. Pat. No. 7,903,020, and FIGS. 2 and 19 from published U.S. Patent Application No. 2013/0139597, which are all hereby incorporated by reference in their entirety for the purpose of teaching such systems.

Aspects of the present disclosure, such as signal transmission, signal detection, and signal processing, may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that aspects of the present disclosure may be practiced with a variety of computer-system configurations, including multiprocessor systems, microprocessor-based or programmable-consumer electronics, minicomputers, mainframe computers, and the like. Any number of computer-systems and computer networks are acceptable for use with the present disclosure.

Specific hardware devices, programming languages, components, processes, protocols, and numerous details including operating environments and the like are set forth to provide a thorough understanding of the present disclosure. In other instances, structures, devices, and processes are shown in block-diagram form, rather than in detail, to avoid obscuring the present disclosure. But an ordinary-skilled artisan would understand that the present disclosure may be practiced without these specific details. Computer systems, servers, work stations, and other machines may be connected to one another across a communication medium including, for example, a network or networks.

As one skilled in the art will appreciate, embodiments of the present disclosure may be embodied as, among other things: a method, system, an apparatus, a device or computer-program product. Accordingly, the embodiments may take the form of a hardware embodiment, a software embodiment, or an embodiment combining software and hardware. In an embodiment, the present disclosure takes the form of a computer-program product that includes computer-useable instructions embodied on one or more computer-readable media.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A portable radar system for vital sign detection, comprising:
processing circuitry configured to transmit a transmit signal from a transmitting antenna at a target selected from the group consisting of a human and an animal such that the transmit signal is reflected by the target to create a reflected signal, wherein the transmit signal and the reflected signal are electromagnetic signals having a wavelength, $\lambda$, where the transmit signal is represented as $T(t)=\cos(\omega t+\phi(t))$ and the reflected signal is represented as $R(t)=\cos(\omega(t-t_d)+\phi(t-t_d))$, where $t_d$ is a time period the transmit signal travels from the transmitting antenna to the target and the reflected signal travels from the target to a receiving antenna;
the processing circuitry configured to receive the reflected signal via the receiving antenna to create a receive signal, wherein the target is vibrating with a first vibration at a first vibration rate and a first vibration amplitude and the first vibration is a respiration of the target, wherein the target is vibrating with a second vibration at a second vibration rate and a second vibration amplitude and the second vibration is a heartbeat, wherein a transmit distance between the transmitting antenna and the target and a receive distance between the target and the receiving antenna are such that $\phi(t-t_d)\approx\phi(t)$ and the receive signal is approximated as $R(t)\approx I(t) \cos(\omega t+\phi(t))+Q(t)\sin(\omega t+\phi(t))$, where $I(t)=\cos(4\pi d/\lambda)$, $Q(t)=\sin(4\pi d/\lambda)$; and
a processor, wherein the processor is configured to:
determine an approximation of the first vibration from a signal representative of R(t);
subtract the approximation of the first vibration from the signal representative of R(t) to produce a remaining signal;
process the remaining signal to produce a processed remaining signal;
analyze the processed remaining signal to identify at least two occurrences of a known position on a cycle of the second vibration in the processed remaining signal corresponding to at least two occurrences of the known position on the cycle of the second vibration, wherein identification of occurrences of the known position on the cycle of the second vibration in the processed remaining signal is enhanced compared to identifying the remaining signal; and
determine the second vibration rate from a corresponding at least two locations of the at least two occurrences of the known position on the cycle of the second vibration in the processed remaining signal; the second vibration rate provided for display.

2. The portable radar system of claim 1, comprising:
a portable radar assembly including the processing circuitry; and
a computing device including the processor, the computing device communicatively coupled to the portable radar assembly.

3. The portable radar system of claim 2, wherein the portable radar assembly comprises a wireless communication module.

4. The portable radar system according to claim 2, wherein the signal representative of R(t) is B(t), wherein B(t) is a baseband signal produced by combining I(t) and Q(t) such that $B(t)=I(t)+jQ(t)=\exp(j4\pi d_0/\lambda)\exp(j(4\pi x_h(t)+4\pi x_r(t)/\lambda)$, where $d=t_d c/2$ and $d=d_0+x_h(t)+x_r(t)$.

5. The portable radar system of claim 4, wherein the processing circuitry comprises a variable gain baseband amplifier configured to amplify the I(t) and Q(t) signals prior to communication to the computing device.

6. The portable radar system of claim 1, wherein the processor is configured to determine the second vibration rate from a corresponding at least two locations of the at least two occurrences of the known position on the cycle of the second vibration in the processed remaining signal.

7. The portable radar system of claim 1, wherein the processor is configured to determine an approximation of the first vibration from the signal representative of R(t) via:
analyzing the signal representative of R(t) to identify at least two occurrences of a known position on a cycle of the first vibration in the signal representative of R(t) corresponding to at least two occurrences of the known position on the cycle of the first vibration; and
separating the signal representative of R(t) into segments between locations of known positions on the cycle of the first vibration in the signal representative of R(t) of the at least two occurrences of the known position on the cycle of the first vibration in the signal representative of R(t) and fitting a curve fit to the first vibration, wherein the curve fit is the approximation of the first vibration.

8. The portable radar system of claim 7, wherein the at least two occurrences of the known position on the cycle of the first vibration in the signal representative of R(t) are at least two peaks of the first vibration in the signal representative of R(t).

9. The portable radar system of claim 8, wherein separating the signal representative of R(t) into segments between peaks of the at least two peaks of the first vibration in the signal representative of R(t) comprises separating the signal representative of R(t) into segments between adjacent peaks of at least two adjacent peaks of the first vibration in the signal representative of R(t).

10. A non-transitory computer readable medium containing a set of instructions that when executed cause processing circuitry to perform a method, wherein the method comprises:
determining an approximation of a first vibration from a signal representative of a reflected signal created by reflection of a transmit signal transmitted at a target selected from the group consisting of a human and an animal, where the transmit signal and the reflected signal are electromagnetic signals having a wavelength, $\lambda$, where the transmit signal is represented as $T(t)=\cos(\omega t+\phi(t))$ and the reflected signal is represented as $R(t)=\cos(\omega(t-t_d)+\phi(t-t_d))$, where $t_d$ is a time period the transmit signal travels from a transmitting antenna to the target and the reflected signal travels from the target to a receiving antenna, where the target is vibrating with the first vibration at a first vibration rate and a first vibration amplitude and the first vibration is a respiration of the target, where the target is vibrating with a second vibration at a second vibration rate and a second vibration amplitude and the second vibration is a heartbeat, where a transmit distance between the transmitting antenna and the target and a receive distance between the target and the receiving antenna are less than 300 m such that $\phi(t-t_d) \approx \phi(t)$ and the receive signal is approximated as $R(t) \approx I(t)\cos(\omega t+\phi(t))+Q(t)\sin(\omega t+\phi(t))$, where $I(t)=\cos(4\pi d/\lambda)$, and $Q(t)=\sin(4\lambda d/\lambda)$;

subtracting the approximation of the first vibration from the signal representative of R(t) to produce a remaining signal;

processing the remaining signal to produce a processed remaining signal;

analyzing the processed remaining signal to identify at least two occurrences of a known position on a cycle of the second vibration in the processed remaining signal corresponding to at least two occurrences of the known position on the cycle of the second vibration, wherein identification of occurrences of the known position on the cycle of the second vibration in the processed remaining signal is enhanced compared to identifying the remaining signal; and determining the second vibration rate from a corresponding at least two locations of the at least two occurrences of the known position on the cycle of the second vibration in the processed remaining signal; the second vibration rate provided for display.

11. The medium according to claim 10, wherein the signal representative of R(t) is B(t), wherein B(t) is a baseband signal produced by combining I(t) and Q(t) such that $B(t)= I(t)+jQ(t)=\exp(j4\pi d_0/\lambda)\exp(j(4\pi x_h(t)+4\pi x_r(t))/\lambda$, where $d=t_d c/2$ and $d=d_0+x_h(t)+x_r(t)$.

12. The medium according to claim 10, wherein determining an approximation of the first vibration from the signal representative of R(t) comprises:

analyzing the signal representative of R(t) to identify at least two occurrences of a known position on a cycle of the first vibration in the signal representative of R(t) corresponding to at least two occurrences of the known position on the cycle of the first vibration;

separating the signal representative of R(t) into segments between locations of known positions on the cycle of the first vibration in the signal representative of R(t) of the at least two occurrences of the known position on the cycle of the first vibration in the signal representative of R(t) and fitting a curve fit to the first vibration, wherein the curve fit is the approximation of the first vibration.

13. The medium according to claim 10, wherein the at least two occurrences of the known position on the cycle of the second vibration in the processed remaining signal are at least two peaks of the second vibration in the processed remaining signal.

14. The medium according to claim 10, wherein the at least two occurrences of the known position on the cycle of the first vibration in the signal representative of R(t) are at least two peaks of the first vibration in the signal representative of R(t).

15. The medium according to claim 10, wherein separating the signal representative of R(t) into segments between peaks of at least two peaks of the first vibration in the signal representative of R(t) comprises separating the signal representative of R(t) into segments between adjacent peaks of the at least two adjacent peaks of the first vibration in the signal representative of R(t).

16. The medium according to claim 10, wherein analyzing the processed remaining signal to identify at least two occurrences of the known position on the cycle of the second vibration in the processed remaining signal corresponding to at least two occurrences of the known position on the cycle of the second vibration comprises analyzing the processed remaining signal to identify at least two adjacent occurrences of the known position on the cycle of the second vibration in the processed remaining signal corresponding to at least two adjacent occurrences of the known position on the cycle of the second vibration.

17. The medium according to claim 10, wherein the at least two occurrences of the known position on the cycle of the second vibration are at least two occurrences of peaks of the second vibration, wherein analyzing the processed remaining signal to identify at least two occurrences of peaks of the second vibration in the processed remaining signal corresponding to at least two occurrences of peaks of the second vibration comprises analyzing the processed remaining signal to identify at least two adjacent occurrences of peaks of the second vibration in the processed remaining signal corresponding to at least two adjacent occurrences of peaks of the second vibration.

18. The medium according to claim 17, wherein determining the second vibration rate from the at least two occurrences of peaks of the second vibration in the processed remaining signal comprises determining the second vibration rate from the at least two adjacent occurrences of peaks of the second vibration in the processed remaining signal.

19. The medium according to claim 10, wherein determining an approximation of the first vibration from the signal representative of R(t) comprises:

analyzing the signal representative of R(t) to identify at least two occurrences of a known position on a cycle of the first vibration in the signal representative of R(t) corresponding to at least two occurrences of the known position on the cycle of the first vibration;

separating the signal representative of R(t) into segments between locations of known positions on the cycle of the first vibration in the signal representative of R(t) of the at least two occurrences of the known position on the cycle of the first vibration in the signal representative of R(t) and fitting a curve fit to the first vibration, wherein the curve fit is the approximation of the first vibration, wherein the at least two occurrences of the known position on the cycle of the first vibration in the signal representative of R(t) are at least two peaks of the first vibration in the signal representative of R(t), wherein the at least two occurrences of the known position on the cycle of the second vibration in the processed remaining signal are at least two peaks of the second vibration in the processed remaining signal.

20. The medium according to claim 10, wherein the first vibration amplitude is larger than the second vibration amplitude.

* * * * *